United States Patent [19]

Paul

[11] Patent Number: 6,149,924
[45] Date of Patent: Nov. 21, 2000

[54] COMPOSITION FOR ENHANCING LIPID PRODUCTION, BARRIER FUNCTION, HYDROGEN PEROXIDE NEUTRALIZATION, AND MOISTURIZATION OF THE SKIN

[75] Inventor: Harbhajan S. Paul, Wexford, Pa.

[73] Assignee: Biomed Research & Technologies, Inc., Wexford, Pa.

[21] Appl. No.: 09/118,909

[22] Filed: Jul. 20, 1998

[51] Int. Cl.[7] .................................................. A61K 7/00
[52] U.S. Cl. .................. 424/401; 424/450; 424/484; 514/2; 514/42
[58] Field of Search .................................. 424/401, 420, 424/484; 512/2, 42

[56] References Cited

U.S. PATENT DOCUMENTS

| | | | |
|---|---|---|---|
| 4,201,235 | 5/1980 | Ciavatta | 132/7 |
| 4,456,596 | 6/1984 | Schaeffer | 424/180 |
| 4,495,079 | 1/1985 | Good | 252/106 |
| 4,732,892 | 3/1988 | Sarpotdar et al. | 514/178 |
| 4,760,096 | 7/1988 | Sakai et al. | 514/847 |
| 4,859,653 | 8/1989 | Morelle elt al. | 514/2 |
| 5,091,171 | 2/1992 | Yu et al. | 424/642 |
| 5,175,190 | 12/1992 | Burton et al. | 514/560 |
| 5,204,099 | 4/1993 | Barbier et al. | 424/301 |
| 5,385,938 | 1/1995 | Yu et al. | 514/557 |
| 5,425,954 | 6/1995 | Thompson et al. | 424/401 |
| 5,470,880 | 11/1995 | Yu et al. | 514/574 |
| 5,472,698 | 12/1995 | Rawlings et al. | 424/401 |
| 5,520,991 | 5/1996 | Eustatiu | 424/195.1 |
| 5,561,158 | 10/1996 | Yu et al. | 514/557 |
| 5,569,461 | 10/1996 | Andrews | 424/405 |
| 5,614,556 | 3/1997 | Cavazza et al. | 514/556 |
| 5,643,899 | 7/1997 | Elias et al. | 514/171 |
| 5,658,580 | 8/1997 | Mausner | 424/401 |
| 5,681,853 | 10/1997 | Yu et al. | 514/557 |
| 5,866,537 | 2/1999 | Bianchi | 514/2 |

FOREIGN PATENT DOCUMENTS

| | | |
|---|---|---|
| 0 722 715 | 7/1996 | European Pat. Off. . |
| 2 581 872 | 11/1986 | France . |
| 2 694 692 | 2/1994 | France . |
| 2 697 750 | 5/1994 | France . |
| WO 96/36348 | 11/1996 | WIPO . |

OTHER PUBLICATIONS

XP–002118778, STN, File Supplier Karlsruhe, DE, File Chemical Abstracts, vol. 66, *American Chemical Soc.*. 1999.
Patent Abstracts of Japan, 61289016 vol. II, No. 159.
Bonte, Frederic et al., "Analysis of all stratum corneum lipids by automated multiple development high performance thin–layer chromatography", *Journal of Chromatography B*, vol. 664; pp. 311–316,(1995).
Ghadially, Ruby et al., "Decreased Epidermal Lipid Synthesis Accounts for Altered Barrier Function in Aged Mice", *Journal of Investigative Dermatology*, vol. 106(5); pp. 1064–1069,(1996).

(List continued on next page.)

*Primary Examiner*—Jose' G. Dees
*Assistant Examiner*—Michael A. Willamson
*Attorney, Agent, or Firm*—Foley & Lardner

[57] ABSTRACT

Increased production of skin lipids, increased barrier function, hydrogen peroxide neutralization, prevention of loss of the natural moisturizing factor from the stratum corneum and moisturization of the skin is provided by a topically applicable composition which includes one or more components selected from the group consisting of branched chain amino acids, derivatives of branched chain amino acids and mixtures thereof, which one or more components are capable of being catabolized in epidermal cells to form lipid precursors for epidermal lipid synthesis. The composition can also include one or more enzyme activators which increase the rate of catabolism of the one or more components.

27 Claims, 4 Drawing Sheets

OTHER PUBLICATIONS

Ghadially, Ruby et al., "The Aged Epidermal Permeability Barrier: Structural, Functional, and Lipid Biochemical Abnormalities in Humans and a Senescent Murine Model", *Journal of Clinical Investigation, Inc.,* vol. 95; pp. 2281–2290,(1995).

Horning, Majorie G. et al., "Fatty Acid Synthesis in Adipose Tissue:II. Enzymatic Synthesis of Branched Chain And Odd–Numbered Fatty Acids", *Journal of Biological Chemistry,* vol. 236(3); pp. 669–672,(1961).

Imokawa, Genji et al., "Decreased Level of Ceramides in Stratum Corneum of Atopic Dermatitis: An Etiologic Factor in Atopic Dry Skin?" *Journal of Investigative Dermatology,* vol. 96(4); pp. 523–526,(1991).

Monger, Daniel J. et al., "Localization of sites of lipid biosynthesis in mammalian epidermis". *Journal of Lipid Research,* vol. 29; pp. 603–612,(1988).

Oku, Hirosuke et al., "Precursor role of branched–chain amino acids in the biosynthesis of iso and anteiso fatty acids in rat skin". *Biochimica et Biophysica Acta,* vol. 1214; pp. 279–287,(1994).

Paul, Harbhajan S. et al., "Effect of carnitine on branched–chain amino acid ocidation by liver and skeletal muscle", *American Physiological Society;* pp. E494–E499,(1978).

Paul, Harbhajan S. et al., "Mechanism of Increased Converson of Branched Chain Keto Acid Dehydrogenase from Inactive to Acitve Form by a Medium Chain Fatty Acid (Octanoate) in Skeletal Muscle", *Journal of Biological Chemistry,* vol. 267(16); pp. 11208–11214,(1992).

Nicolaides, N. "Skin Lipids: Their Biochemical Uniqueness", *Science,* vol. 186; pp. 19–26,(1974).

Rieger, Martin "Ceramides: Their Promise in Skin Care", *Cosmetics & Toiletries,* vol. 111; pp. 35–45, (1996).

Yosipovitch, Gil et al., "Skin Surgace pH: A Protective Acid Mantle", *Cosmetics & Toiletries,* vol. 111; pp. 101–102, (1996).

COMPOSITION FOR ENHANCING LIPID PRODUCTION, BARRIER FUNCTION, HYDROGEN PEROXIDE NEUTRALIZATION, AND MOISTURIZATION OF THE SKIN

FIELD OF THE INVENTION

The present invention relates generally to topically acceptable cosmetic and pharmaceutical compositions. More specifically, it relates to compositions containing branched-chain amino acids and their derivatives and optionally medium-chain fatty acids, and a mixture of vitamins and minerals for enhancing lipid production and improving the barrier functions in the mammalian skin.

BACKGROUND OF THE INVENTION

The skin is the largest organ of the body and protects the body from the environmental damage. This protection is provided by the stratum corneum or horny layer of the skin. In this regard, the stratum corneum acts as a barrier (also known as "water barrier" or "permeability barrier") between the body and the outside environment.

It is now generally accepted that the stratum corneum lipids are the key constituents for a functional barrier. Major classes of stratum corneum lipids include cholesterol, free fatty acids, and ceramides. These lipids are synthesized inside the epidermal cells of the skin and are then secreted into the space between these cells, where they assemble into lamellar bilayer sheets to provide a permeability barrier. The stratum corneum serves as a gate keeper that prevents the entry of infection, chemicals, and other pollutants into the skin. In addition, the stratum corneum prevents the loss of moisture from the skin and thus helps maintain a proper intracellular milieu for normal cellular functions. In addition to providing a permeability barrier, skin lipids are important for the maintenance of the skin's shape, form, and healthy youthful appearance. Therefore, the skin lipid, its integrity, amount, and the ability to renew itself are crucial for esthetic appearance, such as decreasing wrinkles and other signs of aging.

During youth, the blood circulation delivers to the skin all the necessary ingredients for lipid synthesis. However, as we age, the blood flow to the skin decreases. This results in decreased delivery of the lipid building nutrients to the skin. The net result is diminished lipid synthesis and decreased lipid contents of the skin of the aging population (J. Clin. Invest. Vol. 95, pp. 2281–2290, 1995). Depletion and inadequate replenishment of skin lipids leads to moisture loss, dryness, skin wrinkles, and altered appearance. Therefore, restoration of skin's lipid contents is crucial for both health and esthetic reasons.

To improve the skin barrier, publications disclose compositions containing natural or synthetic skin lipids. For example, U.S. Pat. No. 5,643,899 discloses the use of lipids for epidermal moisturization and repair of barrier function. However, it is uncertain whether the lipid composition of these products mimic the composition of the human skin lipids. These products contain only from one to three types of lipids, whereas skin lipids are made up of hundreds of types of lipids. In many instances, lipids in skin care products may have been derived from human and/or animal tissues and thus carry the risk of being contaminated with microorganisms such as viruses and/or bacteria. Furthermore, because lipids in general are unstable, the lipids in these products may undergo peroxidation, and the peroxidation products of lipids may cause harm to the skin. Finally, scientific studies have shown that exogenous lipids, including ceramides, actually impede rather than improve the skin's barrier functions. Because of these limitations and concerns about these products, cosmetic compositions which can enhance endogenous production of a correct mix of a full spectrum of physiological lipids by the epidermal cells are highly desirable.

Skin care compositions are known which include some of the compounds disclosed herein. For example, branched-chain amino acids have been employed in skin treatment composition for the treatment of burns, cuts, abrasions, insect bite, dry skin, psoriasis, dermatitis, eczema, and inflammation (U.S. Pat. No. 5,425,954). Sarpotdar, U.S. Pat. No. 4,732,892 discloses a composition for transdermal penetration enhancers containing branched-chain amino acids. Ciavatt, U.S. Pat. No. 4,201,235 discloses a composition for skin, hair, and scalp conditioners containing several amino acids including the branched-chain amino acids. Morelle, U.S. Pat. No. 4,859,653 discloses the use of derivatives of branched-chain amino acids (butyrylvaline and butyrylleucine) for use in treating wrinkling of the human skin.

The role of branched-chain acyl coenzyme A (CoA) to produce fatty acids in the skin was postulated more than 20 years ago (Nicolaides: Science, 186: 19–26, 1974). However, only recently the incorporation of carbon skeletons of branched-chain amino acids into skin lipids of laboratory animals has been demonstrated (Oku et. al.: Biochim. Biophys. Acta 1214: 279–287, 1994).

The art also discloses other compounds individually used in skin care. For example, U.S. Pat. No. 5,472,698 discloses a composition containing lipid building ingredients (serine or its derivatives). However, these ingredients are capable of producing a single class of skin lipids, namely ceramides, and do not include components to produce a full spectrum of skin lipids, namely cholesterol, free fatty acids, and ceramides.

Similarly, skin care compositions are also known to include caprylic acid (also known as octanoate or octanoic acid), either as free acid, but more often in an esterified form as caprylic/capric acid triglycerides. For example, U.S. Pat. No. 5,175,190 discloses a composition for the treatment of skin lesions containing caprylic/capric triglycerides. U.S. Pat. No. 5,569,461 discloses a topical antimicrobial composition containing a monoester of caprylic acid. U.S. Pat. No. 4,760,096 discloses a moisturizing skin preparation containing caprylic/capric acid triglycerides. U.S. Pat. No. 4,495,079 discloses a composition for facial skin cleanser capable of softening and removing sebum plaque containing a mixture of caprylic acid and capric acid esterified to a fatty alcohol. U.S. Pat. No. 5,472,698 discloses the use of several thiol compounds, including the use of lipoic acid in enhancing lipid production in the skin.

There remains a need, however, for compositions and methods that among other things increase lipid production in the skin.

SUMMARY OF THE INVENTION

Accordingly, it is an object of embodiments of the present invention to provide a skin treatment composition for increasing lipid production in mammalian skin. It is another object of embodiments of the invention to provide a composition for improving the skin condition by improving the performance of the skin barrier. Still another object of embodiments of the invention is to provide a composition for improving the skin condition by increasing the moisture content of the skin. It is yet another object of embodiments of the present invention to provide a composition for neutralizing intracellular toxic products such as hydrogen peroxide ($H_2O_2$). Still another object of the invention is to diminish or even eradicate the appearance of fine skin lines or wrinkles. Still another object of the invention is to diminish or even reverse aging related skin changes. Still another object of embodiments of the invention is to prevent the loss of and even increase Natural Moisturizing Factor in the stratum corneum.

There has been provided according to one aspect of the present invention, a composition for enhancing the production of epidermal lipids, resulting from an admixture which includes: one or more components selected from the group consisting of branched chain amino acids, branched-chain keto acids, derivatives of branched chain amino and keto acids and mixtures thereof as defined below, which one or more components are capable of being catabolized in epidermal cells to form lipid precursors for epidermal lipid synthesis; and one or more enzyme activators which increase the rate of catabolism of the one or more components. In a preferred embodiment, the one or more branched chain amino acids include one or more of L-leucine, L-isoleucine, and L-valine, and the one or more enzyme activators comprise activators selected from the group consisting of octanoic acid, hexanoic acid, alpha keto isocaproic acid, thiamin diphosphate, and alpha chloroisocaproic acid, and their derivatives.

According to another aspect of the present invention, there has been provided a composition for enhancing the production of epidermal lipids, resulting from an admixture which includes: one or more derivatives or metabolites of branched chain amino acids and mixtures thereof, which derivatives or metabolites are selected from the group consisting of: nor-leucine, nor-valine, L-alloisoleucine, L-threoisolucine D,L, or DL-leucine-containing di- and tri-peptides, D,L, or DL- valine-containing di- and tri-peptides, D,L, or DL-isoleucine-containing di- and tri-peptides, nitrogen-free analogues of branched chain amino acids, branched chain alpha-keto acids, isovaleryl-CoA, isovalerylcarnitine, isovaleryglycine, isovaleric acid, beta-methylcrotonyl-CoA, beta-methylcrotonylcarnitine, beta-methylcrotonylglycine, beta-methylcrotonic acid, beta-methylglutaconyl-CoA, beta-methylglutaconylcarnitine, beta-methylglutaconylglycine, beta-methylglutaconic acid, beta-hydroxy-beta-methylglutaryl-CoA, beta-hydroxy-beta-methylglutarylcarnitine, beta-hydroxy-beta-methylglutarylglycine, beta-hydroxy-beta-methylglutaric acid, acetyl-CoA, acetylcarnitine, acetylglycine, acetoacetyl-CoA, acetoacetylcarnitine, acetoacetylglycine, isobutyryl-CoA, isobutyrylcarnitine, isobutyrylglycine, isobutyric acid, methylacrylyl-CoA, methylacrylylcarnitine, methylacrylylglycine, methylacrylic acid, beta-hydroxyisobutyryl-CoA, beta-hydroxyisobutyrylcarnitine, beta-hydroxyisobutyrylglycine, beta-hydroxyisobutyric acid, methylmalonate semialdehyde, propionyl-CoA, propionylcarnitine, propionylglycine, propionic acid, D-methylmalonyl-CoA, L-methylmalonyl-CoA, DL-methylmalonyl-CoA, D-methylmalonylcarnitine, L-methylmalonylcarnitine, DL-methylmalonylcarnitine, D-methylmalonylglycine, L-methylmalonylglycine, DL-methylmalonylglycine, methylmalonic acid, succinyl-CoA, succinylcarnitine, succinylglycine, succinic acid, alpha-methylbutyryl-CoA, alpha-methylbutyrylcarnitine, alpha-methylbutyrylglycine, alpha-methylbutyric acid, tiglyl-CoA, tiglylcarnitine, tiglylglycine, tiglic acid, alpha-methyl-beta-hydroxybutyryl-CoA, alpha-methyl-beta-hydroxybutyrylcarnitine, alpha-methyl-beta-hydroxybutyrylglycine, alpha-methyl-beta-hydroxybutyric acid, alpha-methylacetoacetyl-CoA, alpha-methylacetoacetylcarnitine, alpha-methylacetoacetylglycine, alpha-methylacetoacetic acid, and mixtures thereof; a pharmaceutically acceptable or cosmetically acceptable carrier; and a container for containing the composition prior to application to the skin.

Still another aspect of the invention provides a method of enhancing the production of epidermal lipids, comprising topically applying an effective amount of a composition which comprises one or more components selected from the group consisting of branched chain amino acids, derivatives of branched chain amino acids and mixtures thereof, wherein one or more components are capable of being catabolized in epidermal cells to form lipid precursors for epidermal lipid synthesis and thus to improve skin barrier, to mammalian skin. In a preferred embodiment, the composition of the method includes one or more enzyme activators.

Yet another aspect of the invention provides a method of increasing the catabolism of branched chain amino acids in the epidermis, comprising: providing a topically acceptable composition by admixing an effective amount of one or more enzyme activators in a pharmaceutically or cosmetically acceptable carrier and topically applying the composition to the skin.

Yet another aspect of the invention provides a method of preventing the loss of the natural moisturizing factor in the stratum corneum, comprising topically applying an effective amount of a composition which comprises one or more components selected from the group consisting of branched chain amino acids, derivatives of branched chain amino acids and mixtures thereof, wherein one or more components are capable of being catabolized in epidermal cells to form lipid precursors for epidermal lipid synthesis and improvement of the barrier, to mammalian skin.

Another aspect of the invention provides a method for detoxification of hydrogen peroxide ($H_2O_2$) in the stratum corneum which includes applying an effective amount of the composition according to the present invention to the skin. Still another aspect of the invention provides a method for increasing the vitamin D production which includes applying an effective amount of the composition according to the present invention to the skin. Yet another aspect of the invention provides a method for visibly reducing the appearance of fine skin lines and wrinkles which includes applying an effective amount of the composition according to the present invention to the skin. Still another aspect of the invention provides a method for decreasing aging related skin changes and preferably make skin look more youthful which includes applying an effective amount of the composition according to the present invention to the skin. That is, the present invention acts as an anti-aging agent by its action noted above. Yet another aspect of the invention prevents or eradicates dry skin which includes applying an effective amount of the composition according to the present invention to the skin. Still another aspect of the present invention is to provide a method for increasing the moisture content of the skin by applying an effective amount of the inventive composition to the skin.

Further objects, features and advantages of the present invention will become apparent from consideration of the preferred embodiments which follows.

DETAILED DESCRIPTION OF PREFERRED EMBODIMENTS

As used herein, all percentages are weight percentages based on the total weight of the composition, unless otherwise noted.

The present invention is based, in part, on the discovery that certain biological compounds aid in the lipid production in the skin. Topical application of the present composition will, by enhancing skin lipid production, fortify the lipid barrier, enhance its recovery rate, and provide prolonged and therapeutic moisturization to the skin. The skin thus will have a younger looking or more youthful appearance and fine skin lines and wrinkles may be visibly diminished or even eradicated. The signs of aging thus may be reduced, reversed, slowed or otherwise diminished. That is, the composition has anti-aging effects. The occurence of dry skin will also be diminished or erradicated.

In contrast to the known art, the compositions of the present invention does not require lipids, but contain precursors of lipids. These precursors include a group of lipogenic amino acids, such as branched chain amino acids and their derivatives. In addition, the composition optionally may contain enzyme activators and vitamins to accelerate the metabolism of these amino acids and increase the production skin lipids. All of the ingredients of this composition, being of relatively low molecular weight, readily penetrate into the skin and are utilized for lipid production using the biochemical machinery of the skin cells.

The lipogenic amino acids preferably include any branched chain amino acids (hereinafter BCAAs) capable of being catabolized into small carbon fragments which are used for the synthesis of fatty acids and cholesterol.

Figure 2:
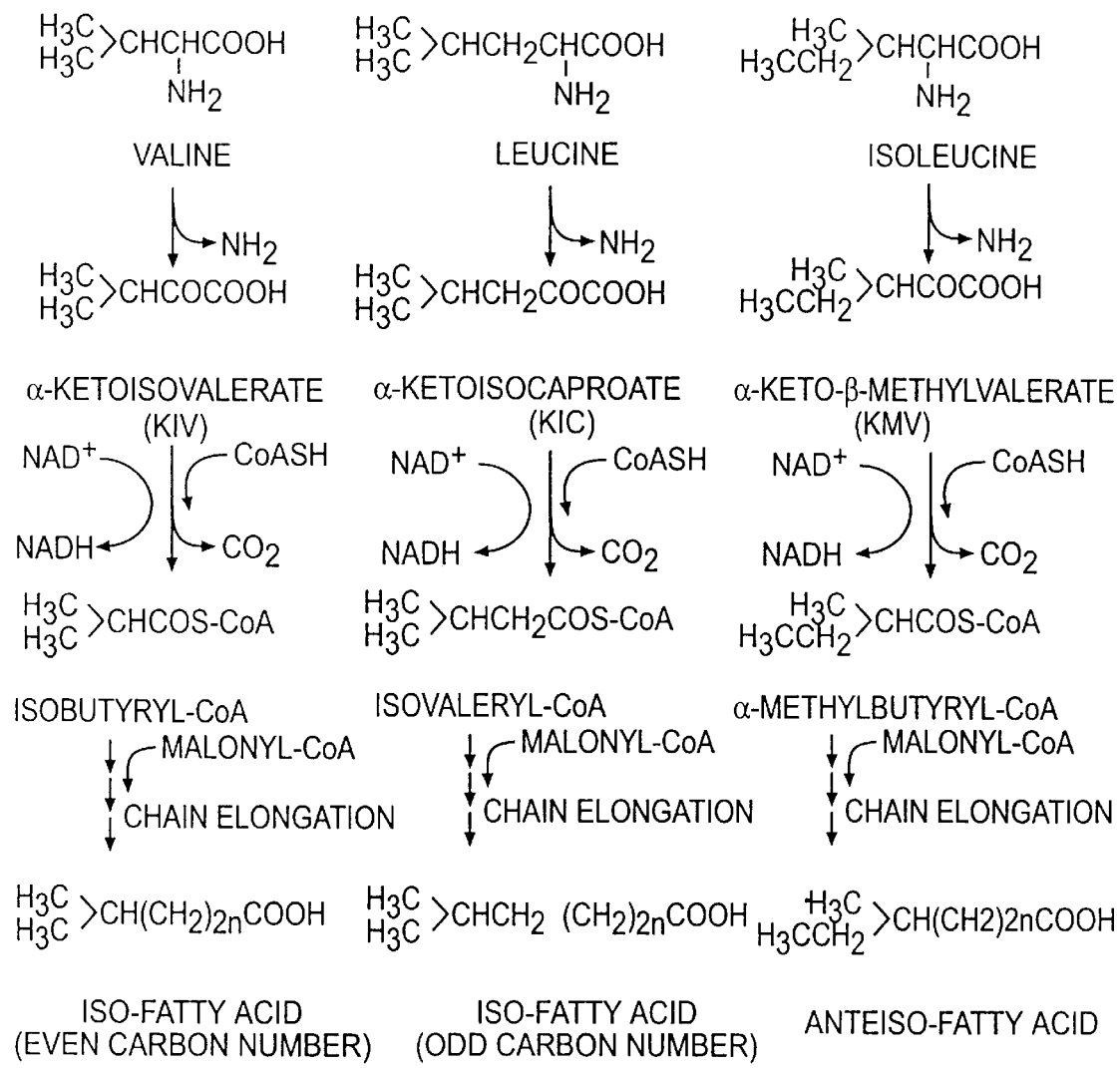
FIG. 2 depicts the synthesis of branched-chain fatty acids from the metabolites of three preferred branched-chain amino acids.

The synthesis of lipids from branched-chain amino acids has been known for tissues such as brain, adipose tissue, liver, and skeletal muscle. However, the use of topically applied branched-chain amino acids to enhance the production of lipids in mammalian skin has not been considered previously. Skin cells have the capacity to transport and degrade branched-chain amino acids into small fragments. These carbon fragments then serve as precursors ("pro-lipids") for skin lipid synthesis. Acyl-CoA intermediates derived from branched-chain amino acids can serve as a "primer" or "starter" for the synthesis and chain elongation of branched-chain fatty acids found in skin lipids. The fatty acid chain is elongated by adding to the "starter" CoA derivative a number of C2 units. These $C_2$ units are derived from malonyl-CoA as shown in FIG. 2 and described in Nicolaides: Science, 186: 19–26, 1974. The development of a skin care product utilizing biological compounds such as BCAAs capable of being metabolized into precursors for skin lipid production, is an important feature of this invention. The amino acids can be used in either their levorotary (L), dextrorotary (D), or racemic (DL) forms.

Preferred BCAAs may include one or more L-leucine, L-valine, L-isoleucine, and mixtures thereof.

Besides the lipogenic, particularly, the branched-chain amino acids, derivatives of amino acids can also be used. The derivatives include analogues of amino acids. Examples of analogues of L-leucine, L-valine and L-isoleucine are:

1. Nor-leucine.
2. Nor-valine.
3. L-alloisoleucine
4. D, L, or DL-Leucine-containing di- and tri-peptides.
5. D, L, or DL-Valine-containing di- and tri-peptides.
6. D, L, or DL-Isoleucine-containing di- and tri-peptides.

Other derivatives, such as nitrogen-free analogues of lipogenic amino acids, particularly BCAAs, such as alpha keto acids and/or mixtures thereof may also be used in the present composition. The following are representatives of alpha keto acids of branched-chain amino acids:

1. Alpha ketoisocaproic acid.
2. Alpha ketoisovaleric acid.
3. Alpha keto beta methylvaleric acid.

In addition, other derivatives such as metabolites or their derivatives derived from lipogenic, particularly branched-chain amino acids, may be incorporated in the composition of the present invention. The following are representative metabolites and derivatives of branched-chain amino acids:

1. Isovaleryl-CoA
2. Isovalerylcarnitine
3. Isovalerylglycine
4. Isovaleric acid
5. Beta-methylcrotonyl-CoA
6. Beta-methylcrotonylcarnitine
7. Beta-methylcrotonylglycine
8. Beta-methylcrotonic acid
9. Beta-methylglutaconyl-CoA
10. Beta-methylglutaconylcarnitine
11. Beta-methylglutaconylglycine
12. Beta-methylglutaconic acid
13. Beta-hydroxy-beta-methylglutaryl-CoA
14. Beta-hydroxy-beta-methylglutarylcarnitine
15. Beta-hydroxy-beta-methylglutarylglycine
16. Beta-hydroxy-beta-methylglutaric acid
17. Acetyl-CoA
18. Acetylcarnitine
19. Acetylglycine
20. Acetic acid
21. Acetoacetic acid
22. Acetoacetyl-CoA
23. Acetoacetylcarnitine
24. Acetoacetylglycine
25. Isobutyryl-CoA
26. Isobutyrylcarnitine
27. Isobutyrylglycine
28. Isobutyric acid
29. Methylacrylyl-CoA
30. Methylacrylylcarnitine
31. Methylacrylylglycine
32. Methylacrylic acid
33. Beta-hydroxyisobutyryl-CoA
34. Beta-hydroxyisobutyrylcarnitine
35. Beta-hydroxyisobutyrylglycine
36. Beta-hydroxyisobutyric acid
37. Methylmalonate semialdehyde
38. Propionyl-CoA
39. Propionylcarnitine
40. Propionylglycine 41. Propionic acid
42. D-methylmalonyl-CoA
43. L-methylmalonyl-CoA
44. DL-methylmalonyl-CoA
45. D-Methylmalonylcarnitine
46. L-Methylmalonylcarnitine
47. DL-Methylmalonylcarnitine
48. D-Methylmalonylglycine
49. L-Methylmalonylglycine
50. DL-Methylmalonylglycine
51. Methylmalonic acid
52. Succinyl-CoA
53. Succinylcarnitine
54. Succinylglycine
55. Succinic acid
56. Alpha-methylbutyryl-CoA
57. Alpha-methylbutyrylcarnitine
58. Alpha-methylbutyrylglycine
59. Alpha-methylbutyric acid
60. Tiglyl-CoA
61. Tiglylcarnitine
62. Tiglylglycine
63. Tiglic acid
64. Alpha-methyl-beta-hydroxybutyryl-CoA
65. Alpha-methyl-beta-hydroxybutyrylcarnitine
66. Alpha-methyl-beta-hydroxybutyrylglycine
67. Alpha-methyl-beta-hydroxybutyric acid
68. Alpha-methylacetoacetyl-CoA
69. Alpha-methylacetoacetylcarnitine
70. Alpha-methylacetoacetylglycine
71. Alpha-methylacetoacetic acid As used herein, the term "derivative of a branched chain amino acid" or "derivatives of BCAA" includes all analogues of BCAAs, such as nitrogen-free analogous, all derivatives, metabolic products and metabolic intermediates of BCAAs, derivatives of the metabolic products of BCAAs, and peptides of BCAAs, such as di- and tri-peptides.

The three preferred branched-chain amino acids, L-leucine, L-valine, and L-isoleucine serve as precursors for lipid synthesis. Catabolism of these branched-chain amino acids results in the production of small carbon fragments which are efficiently utilized for the synthesis of fatty acids and cholesterol.

These three branched-chain amino acids are also believed to have an indirect role in the synthesis of ceramides. As described above, skin is capable of synthesizing a large variety of branched-chain fatty acids utilizing the branched-chain amino acids. Some of these fatty acids have the potential to be incorporated into skin ceramides. The biosynthesis of ceramide in the skin is a two step process. It begins with a reaction between palmitoyl-CoA and the non-essential amino acid, serine. This reaction is catalyzed by the enzyme, serine palmitoyltransferase. The resulting product is 3-ketosphingosine, which then is reduced to form dihydro sphingosine (also known as sphinganine). Next, the addition of an amide-linked fatty acid results in ceramide. It appears that the synthesis of sphingosine in the skin may not be very diligently controlled. A variety of long-chain fatty acyl-CoAs, including the branched-chain fatty acyl-CoAs, can be substituted for palmitoyl-CoA. Thus, branched-chain amino acids have the potential to contribute to the formation of sphingosine. In the second step of ceramide synthesis, fatty acids of varying chain length are utilized for acylation of sphingosine. Branched-chain fatty acids can be substituted for other fatty acids for this acylation reaction. Thus branched-chain amino acids have the possibility of contributing to the amide-linked fatty acid of ceramides. In summary, branched-chain amino acids can contribute to ceramide production in the skin.

Figure 1:
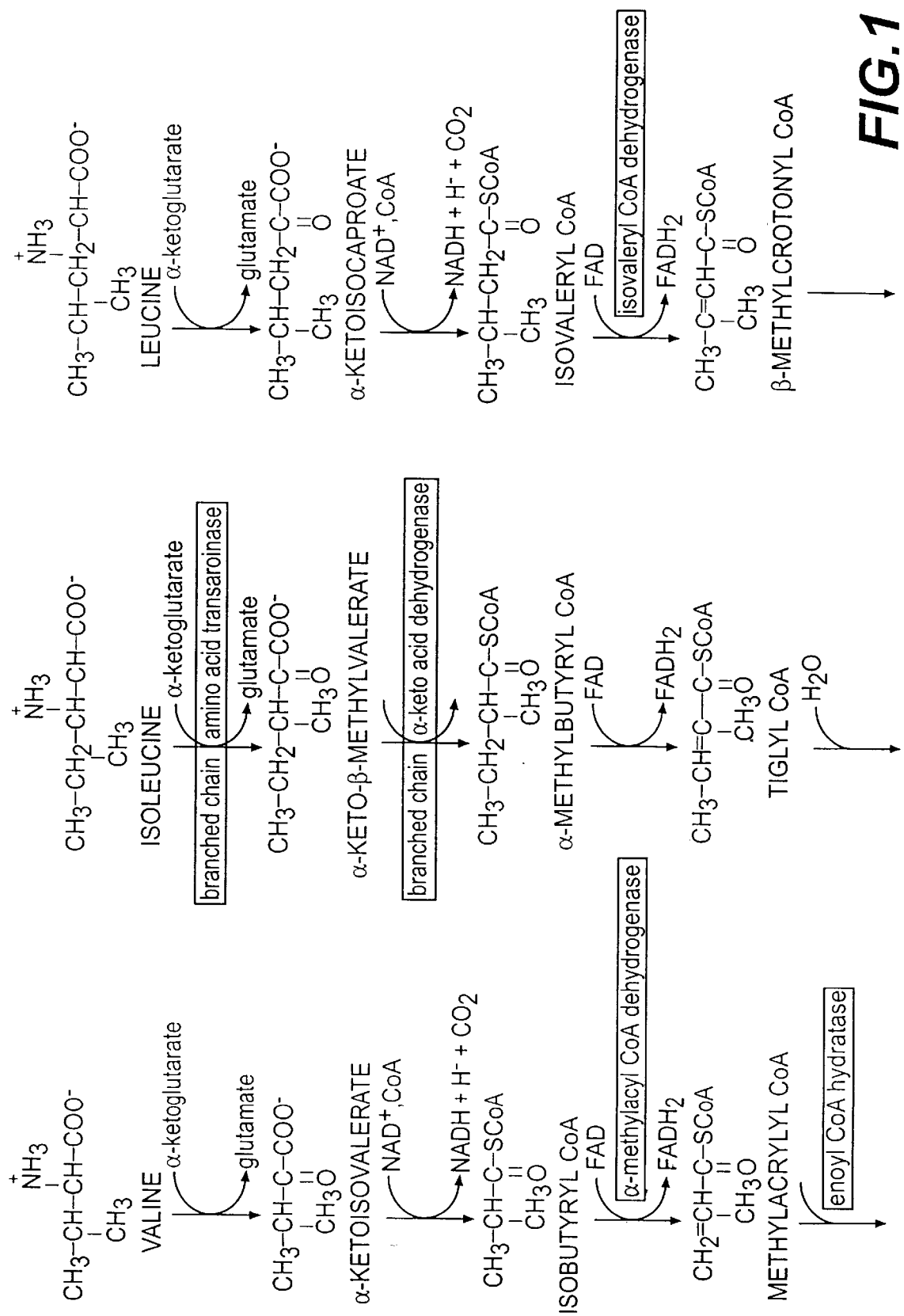
FIG. 1 depicts the metabolic pathway for three preferred branched chain amino acids.
Figure 1:
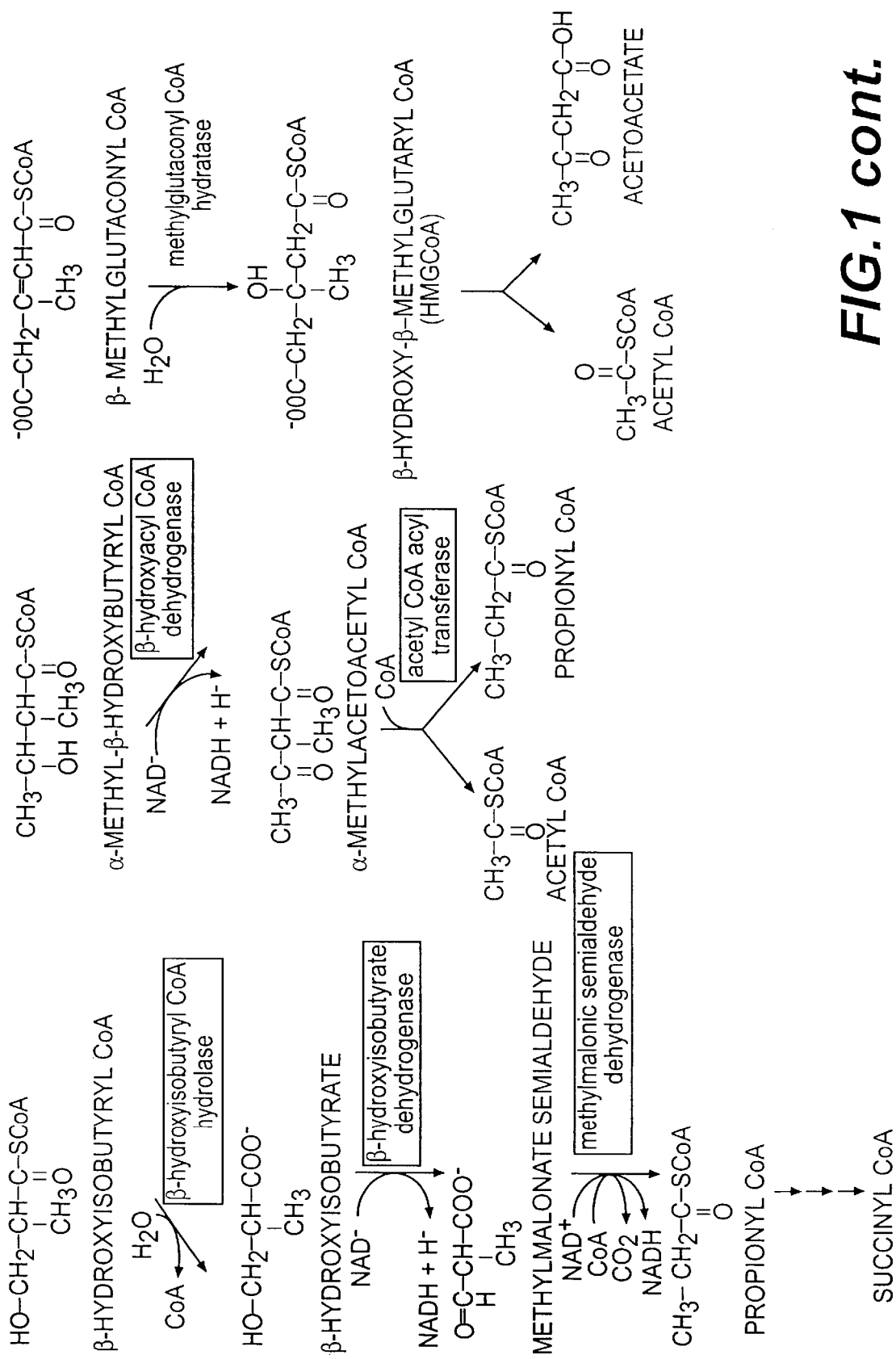

These three branched-chain amino acids are readily transported into the skin cells. Although not intending to be bound by any theory, it is believed that in the cell, these amino acids undergo a transamination reaction which results in the formation of branched-chain keto acids, as shown in FIG. 1. These keto acids comprise alpha ketoisocaproic acid, alpha keto beta methylvaleric acid and alpha ketoisovaleric acid derived from leucine, isoleucine, and valine, respectively. In the next step, all three branched-chain keto acids are oxidatively decarboxylated by a single mitochondrial multienzyme complex known as branched-chain keto acid dehydrogenase. The reaction products of alpha ketoisocaproic acid, alpha keto beta methylvaleric acid, and alpha keto isovaleric acid are isovaleryl-CoA, alpha methylbutyryl-CoA, and isobutyryl-CoA, respectively. These branched-chain acyl-CoAs further undergo a series of biochemical reactions that result in the production of small carbon fragments. The final end products of leucine catabolism are a two carbon acetyl-CoA and a four carbon acetoacetic acid. Acetoacetic acid is further metabolized to yield two molecules of acetyl-CoA. The final end products of isoleucine catabolism are acetyl-CoA and a three carbon propionyl-CoA. Further metabolism of propionyl-CoA results in four carbon succinyl-CoA, which is an intermediate of Krebs cycle. Further metabolism of succinyl-CoA results in citric acid formation. The final end product of valine catabolism is propionyl-CoA, which then is metabolized to succinyl-CoA.

All the end products of branched-chain amino acid metabolism are excellent precursors for fatty acid and cholesterol synthesis. Additionally, one of the intermediates in the leucine catabolic pathway, beta-hydroxy-beta-methyl glutaryl-CoA, is efficiently converted into cholesterol.

Besides utilizing BCAAs for synthesis of lipids in the epidermis, BCAAs are also utilized for the synthesis of lipids in the sebaceous glands. The sebaceous glands utilize BCAAs to synthesize branched-chain fatty acids (BCFA), which then become part of the sebum. Secretion of BCFA-enriched sebum on the skin surface may prevent dehydration of the skin.

Another advantage and use of BCAAs is as follows. A naturally occurring potent moisturizing component known as Natural Moisturizing Factor (NMF) is found in the stratum corneum. NMF serves as an efficient moisturizer because its constituent chemicals are highly water soluble, hygroscopic, and very efficient humectants. It is now well recognized that NMF is a mixture of amino acids and their derivatives. Therefore, BCAAs and their numerous metabolites may increase NMF's constituent chemical pool and thus aid in the skin's moisturization.

Since the metabolism of BCAA is coupled wish the production of alanine, glutamic acid and glutamine in the skin, these amino acids thus can further contribute to increasing the levels of NMF constituents. Additionally, glutamine in the skin is converted to pyrrolidone carboxylic acid, a highly potent humectant.

Another relationship between BCAAs, skin barrier, and NMF is that a stronger barrier will prevent the loss of NMF from the skin, and thus allows maximum moisturization of the skin.

The total amount of each of the BCAAs in the inventive composition generally ranges from 0.001% to 40 wt %, acceptably from 0.01% to 20 wt %, and also acceptably from 0.01% to 10 wt %. However, other concentrations are acceptable, e.g., 0.1 to 5, 0.5 to 5, 1 to 3, 3 to 5, 5 to 7, 10 to 15, 15 to 20 and >20 wt %.

The branched-chain amino acids may be used individually or in combinations of two or more amino acids. When more than one branched-chain amino acids are used, the ratio and proportions between them can be varied using the present specification as a guide, in order to maximize their metabolic potential as lipid precursors. When the three preferred amino acids are used, an acceptable range of weight ratios between L-isoleucine, L-leucine and L-valine is (0.5–1.5):(1–3):(2–6), respectively, with a more acceptable ratio of 1:2:4, respectively.

Besides the small fragments, many metabolites derived from branched-chain amino acids (e.g., acyl-CoA intermediates) serve as primers for the synthesis and chain elongation of straight-chain and branched-chain fatty acids, found in skin lipids. Several of the acyl-CoA intermediates may serve as elongation agents by replacing malonyl-CoA in their reaction with acetyl-CoA.

An important ingredient of the composition are enzyme activators. Enzyme activators are broadly defined herein as any component which by activating an enzyme, such as by allosteric modifications, increases the rate of catabolism of the BCAA. Some BCAAs, in particular, L-leucine, have been found to have an enzyme activation effect. However, this effect is significantly less in comparison to the activators listed below. Accordingly, in the present invention enzyme activators do not include BCAAs. Advantageous activators are selected from the group consisting of octanoic acid, hexanoic acid, alpha keto isocaproic acid, alpha chloroisocaproic acid, thiamin diphosphate and their derivatives and mixtures thereof. The derivatives can include organic salts (e.g., ornithine salts), inorganic salts (e.g., sodium and potassium salts), esters with alcohol or cholesterol, and mono-, di- and triglycerides of octanoic acid or hexanoic acid.

Figure 3:
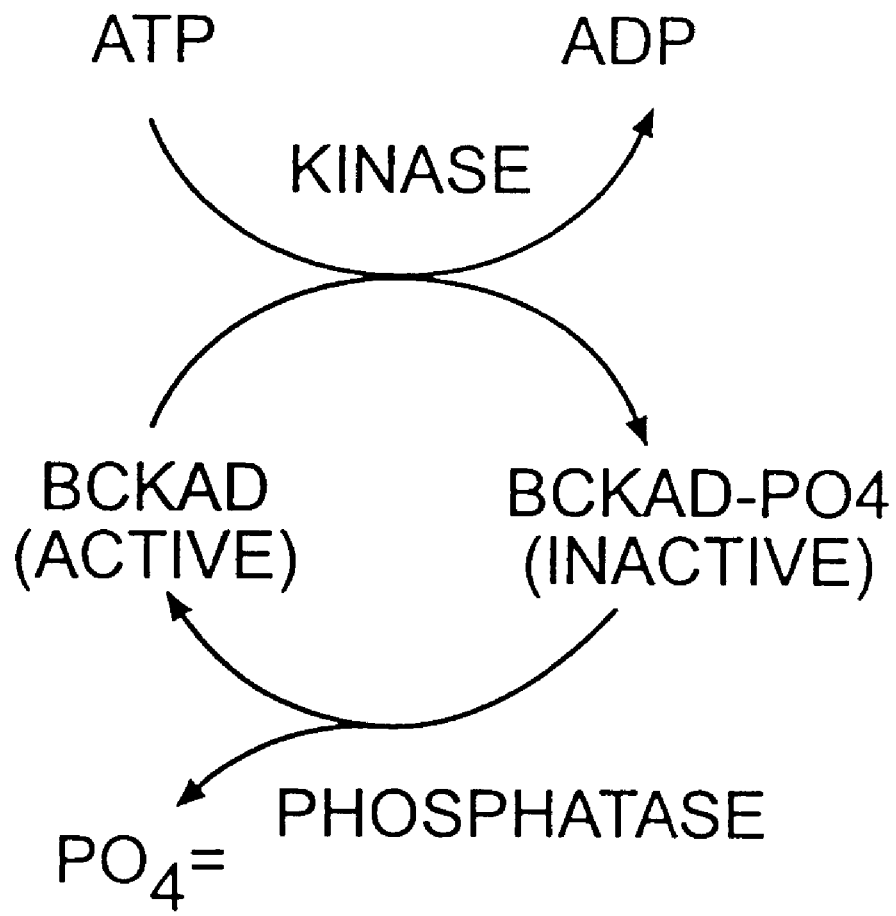
FIG. 3 depicts the inactivation and activation of branched-chain keto acid (BCKA) dehydrogenase by phosphorylation and dephosphorylation, respectively.

The catabolism of branched-chain amino acids is highly regulated. The rate-limiting step for the catabolism of these amino acids is the enzyme branched-chain keto acid dehydrogenase. The activity of this enzyme acts as a "bottleneck" in the pathway that leads to the production of lipid synthesizing precursors from branched-chain amino acids. In most cells, branched-chain keto acid dehydrogenase exists in two forms, an active, dephosphorylated form, and an inactive, phosphorylated form. Phosphorylation and inactivation of branched-chain keto acid dehydrogenase is catalyzed by a specific protein kinase as shown in FIG. 3. The proportion of branched-chain keto acid dehydrogenase in the active, dephosphorylated form varies among various tissues. Only in the active form, the branched-chain keto acid dehydrogenase is capable of catabolizing the branched-chain amino acids.

Those tissues in which branched-chain keto acid dehydrogenase exists largely in an inactive, phosphorylated form, is due to the presence of a large amount of the kinase in these tissues. For example, in the skeletal muscle, a tissue in which branched-chain keto acid dehydrogenase exists largely in an inactive form, there is a high kinase activity. On the other hand, in the liver, where branched-chain keto acid dehydrogenase exists largely in an active form, there is very little kinase activity. Scientific studies have shown that in those tissues where branched-chain keto acid dehydrogenase exists in an inactive or only partially active form, this enzyme can be converted into a fully active form by kinase inhibitors such as the medium-chain fatty acid octanoate (Paul: J. Biol. Chem. 267: 11208–11214, 1992). Inhibition of the kinase blocks the phosphorylation of branched-chain keto acid dehydrogenase, thus maintaining this enzyme into its active form. The net effect is that a fully active form of branched-chain keto acid dehydrogenase can now catabolize branched-chain amino acids at a much faster rate.

In the human skin fibroblasts, approximately 35% of the branched-chain keto acid dehydrogenase exists in the active, dephosphorylated, form (Toshima et. al.: Clin. Chim. Acta 147: 103–108, 1985). This means that under normal metabolic conditions, only a small fraction of the available branched-chain amino acids can be converted into lipid precursors. In order to maximize the production of such precursors from branched-chain amino acids, it is essential to convert branched-chain keto acid dehydrogenase into a fully active form. This can be accomplished by including octanoate in the composition of the present invention. Octanoate readily penetrates into the skin and inhibits the phosphorylation of the branched-chain keto acid dehydrogenase, which results in increased activity of this enzyme. This in turn stimulates catabolism of branched-chain amino acids. The net effect of these changes is increased production of small carbon fragments from branched-chain amino acids, which then are utilized for skin lipid synthesis.

In the present invention, the preferred enzyme activator octanoate may also have other roles. For example, besides functioning as an activator of the branched-chain keto acid dehydrogenase, this fatty acid itself can be incorporated into skin lipids (Adv. Lip. Res. 24: 57–82, 1991). Octanoate can be incorporated into skin lipid by first being converted to octanoyl-CoA and its subsequent metabolism to acetyl-CoA, which then can be used for cholesterol and fatty acid synthesis. Another potential benefit of octanoate in the present invention is that it improves the moisturization of the skin.

The amount of enzyme activator can also be varied depending upon the concentration of the branched-chain amino acids in the formulation of the present invention. In general, the total amount of enzyme activator in the inventive composition ranges from 0.001% to 20%, acceptably from 0.01% to 10%, and also acceptably from 0.1% to 5%. However, other concentrations are acceptable, e.g., 0.1 to 5, 0.5 to 1.0, 1 to 3, 3 to 5, 5 to 7, 10 to 15, 15 to 20 and >20 wt %.

Besides branched-chain amino acids, the non-essential amino acid serine (or its derivatives such as serine-containing dipeptides) may also be used in the present invention. The role of serine or its derivatives is to serve as a building block for the production of skin ceramides. Serine by reacting with palmitoyl-CoA is converted into 3-ketosphingosine, which through a series of reactions is converted into ceramides. Skin cells are capable of converting serine into ceramides. Another advantage of serine is that in the skin, it is metabolized to pyruvate which then produces acetyl-CoA for lipid synthesis.

Optionally, the composition may also contain the amino acids glycine, alanine and threonine. Glycine is converted in the skin to serine, which as noted above serves as a building block for the production of skin ceramides. Alanine is converted in the skin to pyruvate, which as noted above, is used in the production of acetyl-CoA. Threonine is converted in the skin to alpha-ketobutyrate which is useful in acidifying the skin and neutralizing $H_2O_2$. Furthermore, the alpha-ketobutyrate is metabolized to propionyl-CoA which is used in the production of lipids.

Other optional ingredients which may be advantageously employed in this invention are combinations of one or more vitamins. According to a recent study (Annals of New York Acad. Sci., 1993), the majority of people in the U.S. consume diets that fall short of the recommended daily allowances for most vitamins. Such deficient diets make skin cells also deficient with these vitamins and compromise their ability to perform normal metabolism. In general, vitamins are essential for good health and protect the skin cells from damage caused by natural body processes (free radical production), lifestyles (smoking), and environmental stress (chemical pollutants and UV radiation) and aging and photodamaging (Drug & Cosmetic Industry,160: 60–62, 1997; 161: 52–56,1997).

The vitamins usable with the present invention can include one or more of panthenol, pyridoxine, biotin, vitamin E, and mixtures thereof.

In the present invention, a major role of vitamins is to serve as cofactors for many biochemical reactions of branched-chain amino acid metabolism and for reactions necessary for lipid production. Vitamins in the present composition include vitamin $B_5$ (panthenol), vitamin $B_6$(pyridoxine), vitamin H (biotin), and vitamin E. The vitamins are incorporated into the formulation in any suitable form.

Vitamin $B_5$(panthenol) is included as a stable and biologically active analog of pantothenic acid, a vitamin of the B-complex group and a normal constituent of the skin and hair. When panthenol is applied topically, it quickly penetrates into the skin, is readily converted into pantothenic acid, and is incorporated into CoA.

Pantothenic acid improves wound repair and healing. This is due to the effect of pantothenic acid on intracellular protein synthesis and cell proliferation. Thus, it may play a role in the aging skin. Panthenol is a water soluble, non-irritating, and non-sensitizing moisturizing agent. The humectant character of panthenol enables it to hold water or attract water from the environment to yield moisturizing effects to the skin and thus prevents dry skin. Deficiency of pantothenic acid in laboratory animals causes dermatitis.

The role of panthenol in the present invention is several fold. First and foremost, the CoA derived from panthenol aids in the conversion of branched-chain keto acids into their respective acyl-CoA derivatives. CoA is necessary to activate acetate and palmitate to acetyl-CoA and palmitoyl-CoA, respectively. Acetyl-CoA will serve as a substrate for cholesterol and fatty acid synthesis while palmitoyl-CoA will react with serine to initiate the process of ceramide synthesis. Besides the above functions, CoA has several other roles in cellular metabolism. It plays a role in fatty acid metabolism, and in the synthesis of cholesterol, lipids, and proteins. More than 70 enzymes utilize CoA in a variety of metabolic reactions. Additionally, pantothenic acid is a component of phosphopantetheine of fatty acid synthetase, an enzyme important for the synthesis of intracellular lipids (Devlin: Textbook of Biochemistry, 3rd edition, 28:1132, 1992). Taken together, there are many beneficial reasons for including panthenol (vitamin $B_5$) in the composition of the present invention.

Vitamin B or pyridoxine is metabolized intracellulary to pyridoxal phosphate, the coenzyme form of this vitamin. In this form, it functions as a cofactor for several biochemical reactions. Pyridoxine is utilized as a cofactor by more than 60 enzymes. Pyridoxine aids in amino acid metabolism, particularly in the transaminase reaction of the amino acids, including the transamination of branched-chain amino acids. Additionally, pyridoxine plays a role in the synthesis, catabolism, and interconversion of amino acids. Thus, it is essential for the metabolism of nearly all amino acids. In the present invention, the main function of pyridoxine is to facilitate the transamination of branched-chain amino acids, an important first step for their metabolism. Additionally, this vitamin functions as a coenzyme for the serine-palmitoyl-CoA transferase, the rate-limiting enzyme for the synthesis of ceramides in the skin (Devlin: Textbook of Biochemistry, 3rd edition,10:449–456,1992).

An additional advantage of including pyridoxine is that this vitamin is involved in the production of niacin from the amino acid tryptophan. Niacin and its coenzymes nicotinamide adenine dinucleotide (NAD and NADH) and nicotinamide adenine dinucleotide phosphate (NADP and NADPH) are important cofactors for both amino acid and fatty acid metabolism.

The vitamin biotin functions as a cofactor for carboxylation reactions. Thus, this vitamin plays an important role in fatty acid and amino acid metabolism. There are several carboxylation steps in the catabolism of branched-chain amino acids which require biotin. In fact, deficiency of biotin has been shown to disturb the metabolism of leucine, one of the branched-chain amino acids, in laboratory animals (J. Nutr. 122: 1493–1499, 1992). The role of biotin in the present invention is several fold. It is included to serve as a cofactor for a number of carboxylases, such as 3-methylcrotonyl-CoA carboxylase in the leucine catabolic pathway, propionyl-CoA carboxylase in the valine catabolic pathway, and acetyl-CoA carboxylase, the rate-limiting enzyme for fatty acid synthesis. Additionally, biotin is a cofactor for the enzyme pyruvate carboxylase. Through its role in pyruvate carboxylase, biotin is essential for the replenishment of the citric acid cycle metabolites which are essential for normal cellular functions.

Vitamin E is included in this formulation because of its antioxidant properties and its ability to neutralize free radicals. Vitamin E used in this invention is in the form of alpha tocopherol acetate, which is readily bioconverted to free vitamin E in the skin (Drug & Cosmetic Industry: 161: 52–56, 1997). Being an antioxidant, Vitamin E helps block lipid peroxidation and prevents the oxidation of fatty acids and lipids, key components of cellular membranes. Thus, vitamin E provides protection to the skin against peroxide radicals, stabilizes the cell membranes, and promotes normal skin cell functions.

An important property of vitamin E is that it protects against UV damage. It is well known that the UV light induces the production of free radicals in the skin. Exposure to UV light sharply reduces the level of vitamin E in the skin (Drug & Cosmetic Industry: 161: 52–56, 1977). Therefore, addition of vitamin E in composition of the present invention will aid in restoring the vitamin E levels in the skin and protect from the damaging effect of UV radiation (sun exposure).

An additional importance of vitamin E is the fact that the number of melanocytes, the melanin producing cells in the skin, in the elderly is sharply reduced resulting in reduced melanin production (Drug & Cosmetic Industry: 161: 52–56,1997). Since the function of melanin is to protect from the damaging effect of UV radiation, application of vitamin E is believed to provide protection to the skin of the elderly in whom melanin production has declined. Additionally, vitamin E is believed to provide enhanced protection of skin against environmental stress, such as from ozone. Furthermore, vitamin E, being a natural moisturizer, will increase skin hydration, relieve dry skin, and improve skin's smoothness and softness.

Vitamin E also enhances the immune system by suppressing prostaglandins, cellular components of the immune system which are sensitive to oxidation.

Vitamin E being a natural antioxidant will prevent or delay rancidity of not only of skin lipids, but also of fatty acids and oils and their derivatives commonly present in numerous skin care products. Through this action, vitamin E should aid in extending the shelf-life of the topical formulation of the composition of the present invention.

Since the present formulation contains free amino acids, the possible presence of nitrite as a potential contaminant in other cosmetic raw ingredients may result in the formation of nitrosamines, which can be toxic to the skin. Presence of vitamin E in the present formulation will aid as a blocking agent or prevent the formation of nitrosamines in the finished product.

The present invention may optionally include vitamin A or its derivatives such as retinal and retinoic acid. Vitamin A and its derivatives can be present in an amount within the range of 20,000 I.U. to 200,000 I.U. However, other amounts are also contemplated. Vitamin A is necessary for normal growth and development and plays a major role in the differentiation of the epidermal cells. Vitamin A deficiency causes atrophy of the epithelial cells, proliferation of basal cells, and increased growth and differentiation of new cells into horny epithelium. This results in symptoms of dryness and scaliness of the skin, and excessive keratinization. Therefore, vitamin A normalizes dry and photodamaged skin and reduces scaliness. Additionally, vitamin A may improve skin's elasticity and skin thickness. Because damaged epithelial cells are susceptible to an increased infection, Vitamin A acts as an "anti-infection" agent due to its ability to repair cells and stimulate normal cell growth. Additionally, Vitamin A analogs have been shown to retard the aging process of the skin. Studies have shown that topical use of retinoic acid reverses photoaging.

The composition of the present invention may optionally include vitamin $B_1$(thiamin), a vitamin of the B-complex group. Thiamin is converted into thiamin pyrophosphate (also known as thiamin diphosphate), the coenzyme form of this vitamin. In this form, it serves as a cofactor for a number of enzymes, including the branched-chain keto acid dehydrogenase. Thus, inclusion of thiamin in the present formulation, will aid in speeding up the metabolism of branched-chain amino acids, and thus will accelerate skin lipid production. Another advantage of thiamin in the present composition is that its coenzyme, thiamin diphosphate, is an inhibitor of the branched chain keto acid dehydrogenase kinase described above. Through this inhibition, thiamin will aid in the activation of branched chain keto acid dehydrogenese, which then will speed up the metabolism of BCAAs and accelerate skin lipid production.

The composition of the present invention may also optionally include vitamin $B_3$ in the form of niacin or niacinamide. This vitamin is the precursor of nicotinamide adenine dinucleotide (NAD) and nicotinamide adenine dinucleotide phosphate (NADP), cofactors for branched-chain keto acid dehydrogenase and other enzymes involved in fatty acid metabolism. Additionally, niacin and its coenzymes play roles in several energy producing reactions in the skin cells and directly and indirectly aid in lipid production.

The composition of the present invention may optionally include vitamin C (ascorbic acid), an important antioxidant vitamin. The skin levels of vitamin C decline due to aging, smoking, and drug intake. Consequently, skin's ability to detoxify certain toxic chemicals diminishes, resulting in damaged and unhealthy skin. The presence of vitamin C can protect from such damaging effects. By far the most important function of vitamin C is that it is essential for the synthesis of skin collagen.

If present, the total amount of panthenol in the inventive composition generally ranges from 0.001% to 20 wt %, preferably from 0.01% to 10 wt %, and most preferably from 0.1% to 5 wt %.

If present, the total amount of pyridoxine in the present composition generally ranges from 0.001% to 10 wt %, preferably from 0.01% to 5 wt %, and most preferably from 0.1% to 2 wt %.

If present, the total amount of biotin in the inventive composition generally ranges from 0.001% to 3 wt %, preferably from 0.01% to 1.5 wt %, and most preferably from 0.05% to 0.5 wt %.

If present, the total amount of vitamin E in the present composition ranges from 0.001% to 25 wt %, preferably from 0.01% to 15 wt %, and most preferably from 0.1% to 10 wt %.

If present, the total amount of each of the other vitamins is present in an amount of from 0.001 to 10 wt %, preferably 0.01 to 5 wt %, and most preferably from 0.05 to 2.0 wt %.

The composition of the present invention may optionally include a thiol compound. The preferred thiol compound will be DL-lipoic acid (also known as DL-6,8-thioctic acid) or salts thereof. Lipoic acid is a cofactor for branched-chain keto acid dehydrogenase. Thus, the presence of this thiol compound in the present invention will aid in normal branched-chain keto acid dehydrogenase activity necessary for branched-chain amino acid metabolism and lipid production. Additionally, a derivative of lipoic acid, known as alpha-lipoic acid has been shown to be a powerful antioxidant in the skin. Accordingly, this may also be included in the composition of the present invention.

The present invention may optionally include L-carnitine. It is well known that L-carnitine plays an important role in the oxidation of long-chained fatty acids. Research has shown that this compound also increases the oxidation of branched-chain amino acids (Paul: Am. J. Physiol. 234: E494-E499, 1978). Therefore, the presence of this compound in the present formulation will aid in the oxidation of branched-chain amino acids and thus increase the supply of small fragments to be utilized for skin lipid synthesis. Carnitine readily forms esters with CoA compounds, especially those derived from the branched-chain amino acids. Thus, the presence of carnitine is believed to accelerate the metabolism of branched-chain amino acids in a way that is beneficial for skin lipid production. The carnitine can also be provided by several derivatives of carnitine such as acetylcarnitine; propionylcarnitine; hexanoylcarnitine; octanoylcarnitine; and palmitoylcarnitine. The use of octanoylcarnitine has the added advantage of also providing octanoate. The total amount of L-carnitine in the inventive composition will range from 0.001% to 20%, preferably from 0.1% to 10%, and most preferably from 0.1% to 5% by weight of the composition. Additionally, L-carnitine being a strong hygroscopic agent, may improve skin moisturization.

The composition of the present invention may optionally include minerals such as magnesium, and manganese, and mixtures thereof. Both magnesium and manganese ions are activators of beta hydroxy beta methylglutaryl-CoA reductase, the rate-limiting enzyme for cholesterol synthesis (Hoppe-Seyler Z. Physiol. Chem. 363: 1217–1224, 1982). Additionally, magnesium ions convert the branched-chain keto acid dehydrogenase from its inactive form into its active form (Paul, J. Biol. Chem. 267: 11208–11214, 1992). Magnesium ions also serve as a cofactor for beta-methyl crotonyl-CoA carboxylase, which is an enzyme in leucine catabolic pathway. Manganese ions are activators of acetyl-CoA carboxylase, the rate-limiting enzyme for fatty acid synthesis (Thampy & Wakil, J. Biol. Chem. 260: 6318–6323, 1985). Therefore, by including magnesium and/or manganese ions in the composition of the present invention, lipid synthesis in the skin can be increased.

Although all the ingredients of the present invention, being small molecules (e.g., less than 500 Daltons in molecular weight), readily penetrate into the epidermis, their transdermal transport could be optionally further enhanced by including the following into the composition of the present invention:

1. Short-chained alcohols, such as ethanol or iso-propanol (Biochim. Biophys. Acta 1195: 169–179, 1994); and
2. Alpha hydroxy acids, such as 2% glycolic acid.

Besides serving as precursors for lipid synthesis, there are other beneficial effects of branched-chain amino acids and their metabolites. Some examples are provided below:

1. Citric acid production:

The metabolism of the amino acid L-valine, through a series of reactions, produces succinyl-CoA. This compound then enters into the Krebs cycle and is converted to citric acid. This endogenously produced citric acid will serve three roles related to lipid production. First, it would serve as a substrate for the citrate cleavage enzyme producing acetyl-CoA, which is then used for lipogenesis. Second, it would serve as an activator of acetyl-CoA carboxylase, the rate-limiting enzyme in fatty acid synthesis (Triscari & Sullivan, Lipids, 12: 357–363, 1977; Beaty & Lane, J. Biol. Chem. 258: 13043–13050, 1983). Third, citrate helps acidify the intracellular pH, which is beneficial for the barrier functions of the skin.

Although citric acid can be incorporated into the composition of the present invention, because of potential problems of transport and interaction with other ingredients, endogenously produced citric acid is desirable and is likely to perform the above biochemical functions.

2. Conversion of branched-chain keto acid dehydroqenase into its active form:

Another beneficial effect of branched-chain amino acids is that the amino acid L-leucine and its ketoanalogue, alpha ketoisocaproic acid, helps to convert branched-chain keto acid dehydrogenase into its active form (Paul: J. Biol. Chem. 267: 11208–1214, 1992), which then accelerates the metabolism of branched-chain amino acids and provides substrates for skin lipid synthesis. In this context, leucine is not only a substrate for the branched-chain keto acid dehydrogenase, but also its activator.

3. Detoxification of hyrogen peroxide:

Intracellular metabolism of branched-chain amino acids results in the production of branched-chain keto acids, which can neutralize and detoxify hydrogen peroxide produced in the skin. It is believed that the branched-chain keto acids have the capacity to directly neutralize hydrogen peroxide on a 1 to 1 molar basis. This interaction between branched-chain keto acids and hydrogen peroxide inside the skin cell is spontaneous and does not require enzyme catalysis. It is an interaction between the branched-chain keto acids carbonyl group (alpha-keto group) and hydrogen peroxide yielding carbon dioxide and isobutyric acid from alpha-ketoisovaleric acid (derived from valine), alpha-methylbutyric acid from alpha-keto-beta-methylvaleric acid (derived from isoleucine), and isovaleric acid from alpha-ketoisocaproic acid (derived from leucine). Therefore, by removing a toxic agent, such as hydrogen peroxide, the branched-chain amino acids can play a crucial and, perhaps an important, role in the health of the skin. This non-enzymatic reaction between hydrogen peroxide and branched-chain keto acids could conceivably mitigate the oxidative and metabolic stress experienced by the epidermis, particularly when the skin is exposed to sun light, chemicals, and other environmental pollutants.

Exposure to radiation (recreational radiation, such as in tanning salons, and therapeutic radiation, such as to cancer patients) produces free radicals in the skin and is associated with generation of hydrogen peroxide. Therefore, topical application of skin care products containing branched-chain amino and keto acids may prove beneficial to the detrimental effects of radiation to the skin of the above described individuals. Furthermore, as an antidote to hydrogen peroxide, branched-chain amino and keto acids would be expected to reduce or abolish the formation of cytotoxic oxygen-derived free radicals in the skin.

The free acids (isobutyric acid, alpha-methylbutyric acid, and isovaleric acid) produced as a result of the reaction between branched chain keto acid and hydrogen peroxide, have the potential to be activated to their coenzyme A derivatives and further metabolized to yield small acyl-CoA fragments for skin lipid synthesis.

4. Acidification of skin cells:

An additional advantage of a composition containing branched-chain amino acids is that these amino acids themselves, their keto acids, and derived free acids, (isobutyric acid, alpha-methylbutyric acid, and isovaleric acid) are strong acidifying agents and will lower the intracellular pH. Studies have shown that an acidic pH promotes the formation of a competent permeability barrier of the skin than an alkaline pH (Maibach: Cosmetic & Toiletries Magazine, 111: 101–102, 1996). An acidic pH (in the range of 4–6) not only promotes barrier functions, but also fights infection.

The skin of diabetic subjects has been shown to have significantly higher (alkaline) pH than normal subjects. Therefore, in diabetic subjects, an additional advantage of the present composition is to lower the skin pH and prevent skin infections which are more prevalent in diabetic subjects.

5. Protein synthesis:

Branched-chain amino acids can also be used for protein synthesis by the skin. These amino acids being essential nutrients can not be synthesized by the human body. Therefore, their availability, particularly for persons who are on a diet or otherwise malnourished, provide important building blocks for protein synthesis by the skin.

6. Vitamin D Production:

Another benefit of branched-chain amino acid based skin care product is that their metabolism will increase the intracellular pool of cholesterol and other sterols under the skin. These compounds in the presence of sun light can then be converted into vitamin D and other derivatives, all of which are useful for normal cellular functions. A recent study has shown a synergy between vitamin D precursors and ceramides on keratinocyte proliferation and differentiation. In this context increased production of ceramide besides improving the barrier functions will also promote keratinocyte proliferation and differentiation by working in conjunction with vitamin D.

Various types of other active ingredients may also optionally be present in cosmetic formulation compositions of the present invention. Active ingredients in this sense are defined as skin or hair benefit agents other than emollients and other than ingredients that merely improve the physical characteristics of the composition. Although not limited to this category, general examples include sunscreens, tanning agents, skin conditioning and moisturizing agents, anti-dandruff agents, hair conditioners and hair growth stimulants.

Sunscreens include those materials commonly employed to block ultraviolet light. Illustrative compounds are the derivatives of PABA, cinnamate, and salicylate. For example, octyl methoxycinnamate and 2-hydroxy-4-methoxy benzophenone (also known as oxybenzone) can be used. Octyl methoxycinnamate and 2-hydroxy-4-methyl benzophenone are commercially available under the trade marks, Parsol MCX and Benzophenone-3, respectively. The exact amount of sunscreen employed in the emulsion can vary depending upon the degree of protection desired from the sun's UV radiation.

Another preferred optional ingredient includes essential fatty acids (EFAs), i.e., those fatty acids which are essential for the plasma membrane formation of all cells. In keratinocytes, EFA deficiency makes cells hyperproliferative. Supplementation of EFA corrects this. EFAs also enhance lipid production of epidermis and provide lipids for the barrier formation of the epidermis. These essential fatty acids are preferably chosen from linoleic acid, gamma-linoleic acid, homo-gamma-linoleic acid, columbinic acid, arachidonic acid, gamma-linolenic acid, timnodonic acid, hexaenoic acid and mixtures thereof.

The inventive compositions may also preferably include hydroxy acids. Hydroxy acids enhance proliferation and increase ceramide production in keratinocytes, increase epidermal thickness, and increase desquamation of normal skin resulting in smoother, younger looking skin. Additionally, the exfoliating properties of these acids will facilitate the entry of the active compounds into the skin and, by improving the barrier, will mitigate the deleterious effects of the hydroxy acids.

The hydroxy acid can be chosen from alpha-hydroxy acids, beta-hydroxy acids, other hydroxycarboxylic acids (e.g., dihydroxycarboxylic acid, hydroxydicarboxylic acid, hydroxytricarboxylic acid) and mixtures thereof or combination of their stereoisomer (D, L, or DL). See, for example, U.S. Pat. No. 5,561,158 to Yu and Van Scott, which disclose alpha-hydroxy acids useful in this invention.

Preferably, the hydroxy acid is chosen from alpha-hydroxy acids. Even more preferably, the hydroxy acid is chosen from 2-hydroxyoctanoic acid, hydroxylauric acid, lactic acid, and glycolic acid, and mixtures thereof. When stereo isomers exists, L-isomer is most preferred.

Preferably, the amount of the hydroxy acid component present in the composition according to the invention is from 0.01 to 20%, more preferably from 0.05 to 10% and most preferably from 0.1 to 3% by weight.

Surfactants, which are also sometimes designated as emulsifiers, may also be incorporated into cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodoll" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulfate, sodium lauryl ether sulfate, alkyl benzene sulphonate, mono and/or dialkyl phosphates and sodium fatty acyl isothionate.

Amphoteric surfactants include such material as dialkylamine oxide and various types of betaines (such as cocoamido propyl betaine).

Emollients can also be incorporated into cosmetic compositions of the present invention. Levels of such emollients may range from about 0.5% to about 50%, preferably between about 5% and 30% by weight of the total composition. Emollients may be classified under such general chemical categories as esters, fatty acids, and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched-chain fatty esters include 2-ethyl-hexyl myristate, isopropyl stearate and isostearyl palmitate. Acceptable tribasic acid esters include triisopropyl trilinoleate and trilauryl citrate. Acceptable straight-chain fatty esters include lauryl palmitate, myristyl lactate, oleyl eurcate and stearyl oleate. Preferred esters include coco-caprylate/caproate (a blend of coco-caprylate and coco-caproate), propylene glycol myristyl ether acetate, diisopropyl adipate and cetyl octanoate. Suitable fatty alcohols and acids include those compounds having from 10 to 20 carbon atoms. Especially preferred are such compounds such as cetyl, myristyl, palmitate and stearyl alcohols and acids.

Among the polyols which may serve as emollients are linear and branched-chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oils, petroleum jelly, squalene and isoparrafins.

Another category of functional ingredients which can be included in the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances, the thickening function may be accomplished by a material also serving as a silicone or emollient. For instance, silicone gums in excess of centistokes and esters such as glycerol stearate have dual functionality.

Many cosmetic compositions, especially those containing water must be protected against the growth of potentially harmful microorganisms. Preservatives are, therefore, desirable. Suitable preservatives include alkyl ester of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dehydroxyacetate and benzyl alcohol. Preservatives will usually be employed in amounts ranging from about 0.05% to 2% by weight of the composition.

Powders may also be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

The topical composition of the invention can be formulated as a cream or lotion having a viscosity of from 4,000 to 10,000 mpas, a fluid cream having a viscosity of from 10,000 to 20,000 mPas or a cream having a viscosity of from 100,000 mPas or above. The composition can be packaged in a suitable container to suit its viscosity and intended use by the user. For example, a lotion or fluid cream can be packaged in a bottle or a roll-ball applicator or a propellant-driven aerosol device or a container filed with a pump for finger operation. When the composition is a cream, it can simply be stored in a non-deformable bottle or squeeze container, such as a tube or lidded jar. The packaged composition would also typically include instructions providing directions for its use.

The composition of the invention can also be blended with commercially available compositions, such as moisturizing lotions to achieve the benefit of the present invention.

The composition can be applied periodically, e.g., daily, twice daily, weekly, or several times a week. The composition is generally applied for a duration of one week to indefinitely, such often will be applied for a period of 1, 2, 3, 4, 5, 6 or more months. The duration of application can also be applied for an indefinite time period, if desired. It will be appreciated that the results discussed herein will depend upon the amount frequency, and duration of application, with highest amounts and more frequent applications providing accordingly faster results.

Applications of the composition of the present invention

Because of its ability to improve skin barrier, the composition of this invention will be beneficial in the following situations, in addition to those set forth above:

a) Depletion group. This includes individuals whose rate of skin barrier depletes faster than others. Examples include:

1. Individuals whose rate of skin lipid synthesis declines faster than others; examples include, but are not limited to diabetics, smokers, chronic consumers of alcohol, and post-menopausal women.

2. Users of cholesterol-lowering drugs in whom drug-induced inhibition of cholesterol synthesis takes place in certain tissues, including the skin.

3. Individuals receiving radiation therapy, such as those with cancer.

4. Individuals receiving ultraviolet light therapy, such as those with certain skin diseases.

5. Users of tanning salons or tanning equipment.

6. Individuals who tan by exposure to sunlight.

7. Subjects who have had long-term topical corticosteroid application develop depletion of the skin barrier lipids. Therefore, the composition of the present invention may be beneficial to such people.

b) Esthetic group: This includes individuals for whom esthetic appearance of the skin is most important. Examples include:

1. The composition of the present invention by increasing lipid synthesis may reduce fine lines and wrinkles.

2. The composition of the present invention being an efficient and long-lasting moisturizer, should benefit those with fine lines and wrinkles.

3. The composition of the present invention being an efficient and long-lasting moisturizer, should benefit those with frequent dry skin.

c) Occupational group: This includes individuals in whom their occupational duties results in damage to the skin. Examples include:

1. Subjects who require an exceptionally stronger barrier, such as those who are frequently exposed to barrier depleting chemicals and pollutants; examples are workers in chemical plants, gas station attendants, auto repair workers.

2. Individuals requiring frequent washing of hands, such as health care workers, veterinary workers, service workers, beauticians, and barbers.

3. Useful for people engaged in wet occupations.

4. Useful for metal workers.

5. Useful for people likely to be exposed to infection. Examples include persons performing human or animal autopsies, funeral home workers, butchers, and meat handlers, garbage handlers and collectors.

d) Skin damage group:

1. Individuals whose skin is subjected to the damaging effect of depilitation by chemicals, tapes, shaving, waxes, creams, lotions, or laser treatments.

2. The composition of the present invention, by improving this barrier, may reduce, or eliminate, the irritating effects of alpha hydroxy acid, beta hydroxyacid; and retin-A-containing skin products, and thus will be of benefit to users of such products.

3. Users of personal hygiene wipes, such as baby wipes.

e) Therapeutic group: This includes individuals who would benefit from an improved skin. Examples include:

1. The composition of the present invention may be particularly suitable for the aging population especially those with photodamaged skin.

2. Subjects with atopic dermatitis, because they display abnormalities of skin lipids and barrier function.

3. Individuals with highly sensitive skin due to poor barrier.

4. The composition of the present invention may modulate and control the skin delivery of certain therapeutic agents and thus enhance their clinical response. Examples of such therapeutic agents include, but limited to, anti-inflammatory agents, antibiotics, antivirals, antifungals, antihistamines, and antineoplastic agents.

5. Subjects with genetic diseases of the skin or with disorders of amino acid metabolism.

6. Subjects exposed to skin trauma, such as frequent skin dressings, users of ostomy bags and other similar tape-assisted or adhesive-assisted devices and dressings.

7. Individuals exposed to skin trauma from the application and removal of those adhesive devices.

8. For transdermal drug delivery.

9. Another useful application of the inventive composition is for the nursing home population. Bed-bound individuals in nursing homes, hospitals, hospices, or home care, particularly those who are mobility impaired are very susceptible to bed sores (also known as pressure ulcers or decubitus ulcers). These bed sores then lead to infection and are associated with a high degree of morbidity, mortality, and health economic expense. Therefore, the composition of the present invention, with attribute to improve the skin's barrier function, will be a preventive adjunct to those complications for this subject population.

10. Premature infants born under 33 weeks of gestational age.

11. To enhance the lasting effects of topical anesthetics.

12. The skin barrier plays an important role in the immune response of the skin. Therefore, the composition of the present invention by improving the barrier is likely to decrease immune reactions.

13. As a pre- and post-operative skin conditioner.

14. As a pre- and post-laser therapy skin conditioner, particularly for cosmetic surgery.

15. Individuals with incontinence dermatitis.

16. To improve skin barrier in individuals with Raynaud's disease and other microangiopathies.

17. To improve skin moisture and barrier functions in individuals with podiatric skin problems.

18. To improve skin dryness subsequent to removal of orthopedic cases.

f) Veterinary:

1. The present composition may also be employed for use in cattle, particularly the udders and teats of dairy cattle. This product will be an effective bovine teat dip. Its application will improve the natural lipid barrier to foreign matter so as to minimize disruption of the natural defense mechanism against irritation and infection. Because the composition will improve the barrier function of the skin, it will reduce the incidence of infection and associated diseases of the udder, such as mastitis.

g) Miscellaneous:

1. The composition of the present invention is likely to prolong the effect of insect repellents.

2. The composition of the present invention may have application in hair shampoos, scalp, nail, cuticle, and lip-care products.

3. In ladies' mens' pre-shave and after-shave moisturizers.

4. In conjunction with hair growth promoting agents.

5. Users of body hair and skin bleaches.

6. Protection from noxious plants such as "poison ivy."

7. Users of latex products such as gloves to improve the barrier and thereby reduces reactions to skin allergens.

8. Individuals engaged in aquatic sports.

9. Individuals living in cold climates and exposed to cold temperatures.

In one preferred embodiment, a composition of the present invention comprises a mixture of L-leucine, L-isoleucine, L-valine, medium-chain fatty acids (octanoate and/or hexanoate) in an admixture with vitamins. The vitamin composition includes, but not limited to, vitamin $B_5$ (Panthenol), vitamin $B_6$ (Pyridoxine), vitamin H (Biotin), and vitamin E (Alpha Tocopherol Acetate).

In another preferred embodiment, the composition may include other amino acids, such as glycine, serine, alanine, and threonine.

In another preferred embodiment, the composition may further contain other vitamins, such as vitamin A, vitamin C, vitamin $B_1$(thiamin), vitamin $B_3$(niacin), lipoic acid (also known as DL-6,8-thioctic acid), and mixtures thereof. In another embodiment, the composition may contain minerals and trace elements, such as magnesium and/or manganese or their salts. In another embodiment, the composition may contain alpha hydroxy acids, such as glycolic, lactic, citric acid and other similar acids, L-carnitine, and mixtures thereof.

In another aspect, the invention provides a cosmetic and/or pharmaceutical composition containing the composition described above in an admixture with a pharmaceutically or cosmetically acceptable base, and optionally containing other known agents including, but not limited to, viscosity agents, emulsifiers, preservatives. It is possible to add dyes, perfumes, detergents or penetrating agents, in a preferred embodiment of the composition of the invention. The composition, according to this invention, may be present in different embodiments including, but not limited to, creams, lotions, shampoos, gels, sprays, and other similar formulations.

The present invention is generally applicable to the treatment of the mammalian skin including for example humans, domestic pets, livestock, and other farm animals.

An acceptable formulation is as follows:

TABLE A

| INGREDIENT | WEIGHT % |
| --- | --- |
| Branched Chain Amino Acids | 0.24 |
| Other Amino Acids | 0.07 |
| Medium-Chain Fatty Acid | 0.10 |
| Vitamins | 1.55 |
| Emollients | 18.00 |
| Preservatives | 0.70 |
| Deionized Water | 79.34 |
| TOTAL | 100.00 |

EXAMPLES

The following examples are offered for purposes of illustration. They are intended neither to define nor limit this invention in any manner.

Example 1

The ability of this formulation to increase the skin lipid contents.

This example reports measurements of the skin lipid contents following treatment with the formulation of the present invention. An in crease in skin lipid contents would indicate the ability of the composition of the present invention to stimulate skin lipid production.

The test formulation was prepared by combining the amino acids, octanoate, vitamins, preservatives, and other ingredients such as emollients and water to make a cream. This product had previously been tested for safety on human subjects, and its safety was established. The composition of the formulation was as follows is set forth in Table A.

The test was conducted as follows: Eight young, non-smoking, women (aged 32–40 years) were recruited for this study. These women had no medical problems and were not using any medications that might interfere with the study results. The panelists were instructed to stop the use of any other skin care products during the course of this study.

Prior to the application of the test product, skin lipids from both arms were extracted and analyzed to establish the baseline value (Day 0). The test product was then applied to one arm (twice daily, morning and evening), while the other arm served as an untreated control. The application of the test product was randomized, and the study was conducted for three weeks. At the end of three weeks, skin lipids from both arms were again extracted and analyzed (Day 21).

The skin lipids were extracted as outlined by Bonte et. al. (J. Chromatography B, 664:311–316, 1995). Skin lipids were extracted from the inner forearm. Before extraction, the surface of the inner forearm was cleaned with paper towel soaked in 30% ethanol. The lipid extraction employed a 3-cm-diameter glass cylinder with polished edges so that it could be pressed against the skin. Three contiguous sites on the inner forearm were extracted. Five ml of ethanol:cyclohexane, 4:1 by volume, was pipetted into the extraction cylinder. After 1 minute of contact with the skin and gentle agitation of the solvent, the solvent was removed. This extraction was repeated 3 times on each of the three adjacent sites. The extracts from all three sites were combined, dried under a stream of nitrogen, and stored in a freezer until analyzed.

Two classes of skin lipids that are produced exclusively by the epidermal cells of the skin, are cholesterol sulfate and ceramides. Therefore, the analysis was focused on these two classes of skin lipids. Skin lipids were analyzed by an independent laboratory specializing in the analysis of skin lipids.

The skin lipid samples were analyzed by thin-layer chromatography. Twenty×twenty cm glass plates coated with 0.25-mm-thick Silica gel G and a preadsorbant on the lower portion of the plate (Adsorbosil-plus-1; Alltech Associates; Deerfield Ill.) were washed with chloroform:methanol, 2:1, activated in a 110° oven, and the adsorbent was scored into 6-mm-wide lanes.

Dried skin lipid samples were dissolved in 100 μl of chloroform:methanol, 2:1, and 20 μl was used for analysis. The polar lipids, such as cholesterol sulfate and ceramides were resolved by development with chloroform:methanol:water, 40:10:1, to 10 cm, followed by chloroform:methanol:acetic acid, 190:9:1, to 20 cm followed by two developments to the top with hexane:ethyl ether:acetic acid, 70:30:1.

After development, chromatograms were air dried, sprayed with 50% sulfuric acid, and slowly heated to 220° C. on an aluminum slab on a hot plate. After 2 hours, charring was complete, and the chromatograms were allowed to cool prior to quantification by photodensitometry. Lipid contents are expressed as microgram per sample and the results are shown in Table I.

TABLE I

Results of Skin Lipid Analysis
Results are Mean ± SEM of 7 subjects

| Lipid Class | Control Arm | | Treated Arm | |
| --- | --- | --- | --- | --- |
| | Day 0 | Day 21 | Day 0 | Day 21 |
| | (Micrograms per sample) | | | |
| Cholesterol | 11.3 ± 1.64 | 14.8 ± 1.45 | 9.7 ± 0.87 | 16.2 ± 1.85 |
| Sulfate | 100% | 131% | 100% | 167% |
| Total Ceramides | 123.0 ± 25.35 | 118.3 ± 15.15 | 107.0 ± 15.54 | 183.6 ± 50.98 |
| % | 100% | 96% | 100% | 172% |

As can be seen from Table I, after merely three weeks of treatment, there was a significant increase in the cholesterol sulfate content in the treated arm than in the untreated control arm. Similarly, there was a significant increase in the ceramide contents of the treated arm than the untreated control arm.

From these results it can be concluded that the composition of the present invention is capable of increasing the production of skin lipids in humans.

Example 2

The ability of the present invention to improve the skin barrier functions.

This example illustrates measurements of the rate of water loss from the skin's surface. This technique is also known as trans epidermal water loss (TEWL). The greater the improvement in the barrier function, the lower the rate of water loss.

The test formulation was the same formulation as in Example 1.

The test was conducted as follows: Eight postmenopausal women (aged 50 to 77 years), who were smokers, but not on estrogen replacement therapy, were recruited for the study. These women had no medical problems and were not using any medications that might interfere with the study results. The panelists were instructed to stop the use of any other skin care products during the course of this study. The study was conducted by an independent testing laboratory, specializing in evaluating the effects of skin care products on humans.

Prior to the application of the test product, the rate of water loss was measured to establish the baseline value. The test product was then applied to one leg (twice daily, morning and evening), while the other leg served as an untreated control. The application of the test product was randomized, and the study was conducted for three weeks. At the end of three weeks, the rate of water loss was measured in both legs before damaging the barrier by tape stripping (pre-stripping). Next, the skin barrier was damaged on both the treated leg and the untreated control leg with an equal number of tape strippings, and the rate of water loss in both legs was again measured (post-stripping). Under normal conditions, the rate of water loss is quite low and it is difficult to reduce it further. Therefore, in assessing the effect of a skin care product on the barrier function, it is customary to increase the rate of water loss by damaging the skin's barrier.

The skin barrier was damaged by tape stripping, which was performed as follows: Two sites (1"×3"), located on the outer side of each lower leg, were stripped. Duct tape, which was cut into 1"×3" strips was used to strip the sites. Both sites on an individual were stripped the same number of times, and stripping was done until at least one of the sites reached a water loss level greater than 20 $g/m^2/h$.

The rate of water loss was measured with a Servo Med Computerized Evaporimeter. This instrument includes a hand held probe which is attached by a cable to a portable electronic display unit. The probe consists of an open cylinder, 15.5 mm long, with a mean diameter of 12.5 mm. Two sensors with the probe measure the temperature and relative humidity at two fixed points, approximately 4 mm apart, along the axis normal to the skin surface. This arrangement is such that the device can electronically derive a value that corresponds to evaporative water loss expressed in $g/m^2/h$.

The data from the evaporimeter are collected by a data collection system utilizing a software. The application program captures the water loss data from the attached evaporimeter at a sampling rate of 5 inputs/second. These inputs are graphed as a real time display on the computer monitor. The extracted value refers to the average evaporative water loss rate collected over a 20 second interval once steady state conditions are achieved.

At each session, duplicate water loss readings were taken from each test site and electronically recorded such that the average value for each test site is computed. Such measures provide a noninvasive method for determining the barrier function of the stratum corneum. Damage leads to a disruption of the barrier which is accompanied by elevated water loss rates. The results of water loss are shown in Table II.

TABLE II

Rate of Water Loss ($g/m^2/h$)

| change | Untreated control site | Treated control site | Net |
| --- | --- | --- | --- |
| Baseline | 3.65 | 3.52 | |
| Day 21 | 3.06 | 3.66 | |

TABLE II-continued

Rate of Water Loss (g/m²/h)

| change | Untreated control site | Treated control site | Net |
|---|---|---|---|
| (pre-stripping) Day 21 (post-stripping) | 22.35 | 12.11 | 10.24 |

It is quite clear from the results in Table II, that the extent to which the water loss rate increased was more pronounced on the untreated control sites compared to their respective treated sites (22.35 vs 12.11). These results are consistent with an improvement in skin barrier in the treated leg. From these results it can be concluded that the composition of the present invention markedly improves the skin barrier. It can also be concluded that the treatment with the composition of the present invention made the skin less vulnerable to repeated tape trauma in which the stratum corneum barrier is mechanically disrupted.

Example 3

The ability of this formulation to increase and maintain the level of skin moisturization.

This example illustrates measurements of skin conductance following treatment with formulation in accordance with the invention. Skin conductance is a measure of the water content of the stratum corneum, and higher the mean conductance, the higher the water content of the skin and more potent the moisturizer.

The test formulation was the same composition prepared according to Example 1.

The test was conducted as follows: Eight post-menopausal women (aged 50 to 77 years), who were smokers, but not on estrogen replacement therapy, were recruited for the study. These women had no medical problems and were not using any medications that might interfere with the study results. The panelists were instructed to stop the use of all moisturizing products during the course of this study. The study was conducted by an independent testing laboratory, specializing in evaluating the effects of skin care products on humans.

Prior to the application of the test product, skin conductance was measured to establish the baseline value. The test product was then applied to one leg (twice daily, morning and evening), while the other leg served as an untreated control. The application of the test product was randomized, and the study was conducted for three weeks. At the end of three weeks, a regression study was performed to determine if the moisturizing effect is maintained after the subjects had discontinued the application of this product.

An IBS Skicon-200 Conductance Meter with a high sensitivity Measurement Technologies Probe was used to measure changes in skin surface hydration levels. Readings based on a series of five successive measurements from each leg were averaged to give a single value at each time. Skin conductance was measured every week for three weeks (Treatment), and again on Days 1, 3, and 6 after discontinuation of the application of the formulation (Regression). The value recorded represents the AC conductance 5 seconds after placing the spring-loaded probe tip to the sample site and are mean of 8 subjects. The results are shown in Table III.

TABLE III

|  | Untreated Control | Treated | Net Change |
|---|---|---|---|
| Baseline Treatment | 87.40 | 81.90 | — |
| Day 7 | 117.75 | 143.28 | 25.53 |
| Day 14 | 98.15 | 153.20 | 55.05 |
| Day 21 Regression | 143.20 | 222.08 | 78.88 |
| Day 22 (Regression Day 1) | 112.40 | 174.60 | 62.20 |
| Day 24 (Regression Day 3) | 117.97 | 186.00 | 68.03 |
| Day 27 (Regression Day 6) | 118.97 | 140.13 | 21.16 |

As can be seen from Table III, during the three weeks (Days 7, 14, and 21) of treatment period, the skin moisture levels were significantly and markedly higher in the treated leg than the untreated control leg. In fact, there was a progressive increase in the moisture content of the skin during the course of this three week study. More significantly, the skin moisture levels remained high for up to 6 days even after treatment had been discontinued. From these results it can be concluded that the composition of the present invention is both an effective and long-lasting moisturizer.

Thus, the present composition can increase the moisture level in the skin by 10 to greater than 100% compared to untreated skin, acceptably from 20%–80%, also acceptably from 20%–60%, when measured at one, two or three weeks.

Similar studies were also performed with three other groups (post-menopausal, non-smoking women, aged 51–79 years; young smoking women, aged 30–41 years; young non-smoking women, aged 32–40 years), and in each case similar results were obtained as reported above in Table III.

Other embodiments of the invention will be apparent to those skilled in the art from consideration of the specification and practice of the invention disclosed herein. It is intended that the specification be considered as exemplary only, with the true scope and spirit of the invention being indicated by the following claims.

All documents referred to herein are expressly incorporated by reference in their entireties.

What is claimed is:

1. A topical composition for enhancing the production of epidermal lipids, resulting from an admixture comprising:
   one or more components selected from the group consisting of L-leucine, L-isoleucine and L-valine, derivatives of L-leucine, L-isoleucine and L-valine and mixtures thereof, which one or more components are capable of being catabolized in epidermal cells to form lipid precursors for epidermal lipid synthesis; and
   one or more enzyme activators selected from the group consisting of octanoic acid, hexanoic acid, alpha keto isocaproic acid, alpha chloroisocaproic acid, thiamin diphosphate, and derivatives thereof, which one or more enzyme activators increase the rate of catabolism of the one or more components; and wherein the one or more components are present in an amount ranging from 0.001 to 40 wt %, based on the weight of the composition; and the one or more enzyme activators are present in an amount ranging from 0.001 to 20 wt %, based on the weight of the composition.

2. A composition as claimed in claim 1, wherein the enzyme activators are capable of converting the branched-chain keto acid hydrogenase from its inactive form into its active form.

3. A composition as claimed in claim 1, wherein the one or more enzyme activators comprise octanoic acid and its derivatives.

4. A composition as claimed in claim 1, wherein the composition further comprises a pharmaceutically or cosmetically acceptable carrier.

5. A composition as claimed in claim 4, wherein the pharmaceutically or cosmetically acceptable carrier comprises one or more of emulsifiers, thickeners, preservatives, powders and coloring agents.

6. A composition as claimed in claim 1, wherein the composition further comprises one or more of serine, glycine, alanine and threonine.

7. A composition as claimed in claim 1, wherein the composition further comprises one or more vitamins.

8. A composition as claimed in claim 7, wherein the one or more vitamins comprise panthenol, pyridoxine, biotin, vitamin E, vitamin A and its derivatives, vitamin $B_1$, vitamin $B_3$ and vitamin C.

9. A composition as claimed in claim 1, wherein the composition further comprises thiol.

10. A composition as claimed in claim 1, wherein the composition further comprises L-carnitine.

11. A composition as claimed in claim 1, wherein the composition further comprises hydroxy acids.

12. A composition as claimed in claim 11, wherein the hydroxy acids are present in an amount of from 0.01 to 20 wt %.

13. A method of enhancing the production of epidermal lipids, comprising:
topically applying an effective amount of the composition of claim 1 to mammalian skin in an amount and for a period of time sufficient to enhance the production of epidermal lipids.

14. A method according to claim 13, wherein the composition is applied for a period of time sufficient to reduce or even eradicate dry skin.

15. A method of increasing the skin lipid synthesis of an individual whose skin is exposed to lipid depleting agents, comprising:
topically applying an effective amount of the composition of claim 1 to the skin of the individual in an amount and for a period of time sufficient to increase skin lipid synthesis.

16. A method of increasing the skin lipid synthesis of an individual taking cholesterol lowering drugs, comprising:
topically applying an effective amount of the composition of claim 1 to the skin of the individual in an amount and for a period of time sufficient to increase skin lipid synthesis.

17. A method of reducing bed sores by increasing the skin lipid synthesis of a mobility impaired individual, comprising:
topically applying an effective amount of the composition of claim 1 to the skin of the individual in an amount and for a period of time sufficient to reduce bed sores.

18. A method of preventing skin damage caused by exposure to UV radiation, by increasing the skin lipid synthesis, comprising:
topically applying an effective amount of the composition of claim 1 to the skin of an individual exposed to UV radiation in an amount and for a period of time sufficient to prevent skin damage caused by exposure to UV radiation.

19. A method for reducing or eradicating the visible appearance of fine skin lines and wrinkles, comprising:
topically applying an effective amount of the composition of claim 1 to the skin of the individual in an amount and for a period of time sufficient to reduce or eradicate the visible appearance of fine skin lines and wrinkles.

20. A method of preventing and/or treating mastitis in dairy cattle, comprising:
topically applying a therapeutically effective amount of the composition of claim 1 to the teats of dairy cattle in an amount and for a period of time sufficient to prevent and/or treat mastitis.

21. A topical composition for enhancing the production of epidermal lipids, resulting from an admixture comprising:
0.001 to 40 wt % based on the weight of the composition of one or more derivatives or metabolites of L-leucine, L-isoleucine, and L-valine and mixtures thereof, which derivatives or metabolites are selected from the group consisting of:
nor-leucine, nor-valine, L-alloisoleucine, L-threoisoleucine, D, L, or DL-leucine-containing di- and tri-peptides, D, L or DL- valine-containing di- and tri-peptides, D, L or DL-isoleucine-containing di- and tri-peptides, nitrogen-free analogues of L-leucine, L-isoleucine and L-valine, branched chain keto acids derived from L-leucine, L-isoleucine, and L-valine, isovaleryl-CoA, isovalerylcarnitine, isovalerylglycine, isovaleric acid, beta-methylcrotonyl-CoA, beta-methylcrotonylcarnitine, beta-methylcrotonylglycine, beta-methylcrotonic acid, beta-methylglutaconyl-CoA, beta-methylglutaconylcarnitine, beta-methylglutaconylglycine, beta-methylglutaconic acid, beta-hydroxy-beta-methylglutaryl-CoA, beta-hydroxy-beta-methylglutarylcarnitine, beta-hydroxy-beta-methylglutarylglycine, beta-hydroxy-beta-methylglutaric acid, acetyl-CoA, acetylcarnitine, acetylglycine, acetoacetyl-CoA, acetoacetylcarnitine, acetoacetylglycine, isobutyryl-CoA, isobutyrylcarnitine, isobutyrylglycine, isobutyric acid, methylacrylyl-CoA, methylacrylylcarnitine, methylacrylylglycine, methylacrylic acid, beta-hydroxyisobutyryl-CoA, beta-hydroxyisobutyrylcarnitine, beta-hydroxyisobutyrylglycine, beta-hydroxyisobutyric acid, methylmalonate semialdehyde, propionyl-CoA, propionylcarnitine, propionylglycine, propionic acid, D-methylmalonyl-CoA, L-methylmalonyl-CoA, DL-methylmalonyl-CoA, D-methylmalonylcarnitine, L-methylmalonylcarnitine, DL-methylmalonylcarnitine, D-methylmalonylglycine, L-methylmalonylglycine, DL-methylmalonylglycine, methylmalonic acid, succinyl-CoA, succinylcarnitine, succinylglycine, succinic acid, alpha-methylbutyryl-CoA, alpha-methylbutyrylcarnitine, alpha-methylbutyrylglycine, alpha-methylbutyric acid, tiglyl-CoA, tiglylcarnitine, tiglylglycine, tiglic acid, alpha-methyl-beta-hydroxybutyryl-CoA, alpha-methyl-beta-hydroxybutyrylcarnitine, alpha-methyl-beta-hydroxybutyrylglycine, alpha-methyl-beta-hydroxybutyric acid, alpha-methylacetoacetyl-CoA, alpha-methylacetoacetylcarnitine, alpha-methylacetoacetylglycine, alpha-methylacetoacetic acid, and mixtures thereof;

0.001 to 20 wt %, based on the weight of the composition of one or more enzyme activators selected from the group consisting of octanoic acid, hexanoic acid, alpha keto isocaproic acid, alpha chloroisocaproic acid, thiamin diphosphate, and derivatives thereof, which one or more enzyme activators increase the rate of catabolism of the one or more derivatives or metabolites:

a pharmaceutically acceptable or cosmetically acceptable carrier; and a container for containing the composition prior to application to the skin.

22. A composition as claimed in claim 21, wherein the nitrogen-free analogues of branched chain amino acids are alpha keto acids and mixtures thereof which are selected from alpha ketoisocaproic acid, alpha ketoisovaleric acid, and alpha keto beta methylvaleric acid.

23. A method of increasing the catabolism of L-leucine, L-isoleucine, and L-valine in the epidermis, comprising:

providing a topically acceptable topical composition by admixing 0.001 to 20 wt % based on the weight of the composition of one or more enzyme activators selected from the group consisting of octanoic acid and its derivatives, hexanoic acid and its derivatives, and alpha keto-isocaproic acid and its derivatives, and 0.001 to 40 wt % based on the weight of the composition of one or more components selected from the group consisting of L-leucine, L-isoleucine, and L-valine, derivatives of L-leucine, L-isoleucine, and L-valine and mixtures thereof, which one or more components are capable of being catabolized in epidermal cells to form pro-lipids for epidermal lipid synthesis, in a pharmaceutically or cosmetically acceptable carrier; and topically applying the topically acceptable topical composition to the skin in an amount and for a period of time sufficient to increase the catabolism of L-leucine, L-isoleucine, and L-valine in the epidermis.

24. A method of enhancing the production of epidermal lipids, comprising:

topically applying an effective amount of a topical composition which comprises 0.001 to 40 wt % based on the weight of the composition of one or more components selected from the group consisting of L-leucine, L-isoleucine, and L-valine, derivatives of L-leucine, L-isoleucine, and L-valine and mixtures thereof, which one or more components are capable of being catabolized in epidermal cells to form pro-lipids for epidermal lipid synthesis, and 0.001 to 20 wt %, based on the weight of the composition of one or more enzyme activators selected from the group consisting of octanoic acid, hexanoic acid. alpha keto isocaproic acid, alpha chloroisocaproic acid, thiamin diphosphate, and derivatives thereof, which one or more enzyme activators increase the rate of catabolism of the one or more components;

to mammalian skin in an amount and for a period of time sufficient to enhance the production of epidermal lipids.

25. A method of increasing the cellular level of the natural moisturizing factor in the stratum corneum, comprising:

topically applying an effective amount of a topical composition which comprises:

0.001 to 40 wt % based on the weight of the composition of one or more components selected from the group consisting of L-leucine, L-isoleucine, and L-valine, derivatives of L-leucine, L-isoleucine, and L-valine and mixtures thereof, which one or more components are capable of being catabolized in epidermal cells to produce metabolites and other amino acids, and 0.001 to 20 wt %, based on the weight of the composition of one or more enzyme activators selected from the group consisting of octanoic acid, hexanoic acid, alpha keto isocaproic acid, alpha chloroisocaproic acid, thiamin diphosphate, and derivatives thereof, which one or more enzyme activators increase the rate of catabolism of the one or more components to mammalian skin in an amount and for a period of time sufficient to increase the cellular level of natural moisturizing factor in the stratum corneum.

26. A method for increasing the production of vitamin D in the skin, comprising:

topically applying an effective amount of a topical composition which comprises 0.001 to 40 wt % based on the weight of the composition of one or more components selected from the group consisting of L-leucine, L-isoleucine, and L-valine, derivatives of L-leucine. L-isoleucine, and L-valine and mixtures thereof, which one or more components are capable of being catabolized in epidermal cells to increase the production of cholesterol and other sterols in the skin, and 0.001 to 20 wt % based on the weight of the composition of one or more enzyme activators selected from the group consisting of octanoic acid, hexanoic acid, alpha keto isocaproic acid, alpha chloroisocaproic acid, thiamin diphosphate, and derivatives thereof, which one or more enzyme activators increase the rate of catabolism of the one or more components, wherein the one or more components selected from the group consisting of L-leucine, L-isoleucine, and L-valine, derivatives of L-leucine, L-isoleucine, and L-valine and mixtures thereof, and the enzyme activators are present in an amount and for a period of time sufficient to increase the production of cholesterol and other sterols in the skin; and exposing the skin to sunlight for a period of time sufficient to increase the production of vitamin D.

27. A method of neutralizing and detoxifying hydrogen peroxide by increasing the intra-cellular level of branched chain keto acids derived from L-leucine, L-isoleucine, and L-valine, comprising:

topically applying an effective amount of a topical composition which comprises 0.001 to 40 wt % based on the weight of the composition of one or more components selected from the group consisting of L-leucine, L-isoleucine, and L-valine, derivatives of L-leucine, L-isoleucine, and L-valine and mixtures thereof, which one or more components are capable of being catabolized in epidermal cells to produce branched-chain keto acids derived from L-leucine, L-isoleucine, and L-valine and 0.001 to 25 wt % based on the weight of the composition of vitamin E;

to the skin of an individual in an amount and for a period of time sufficient to increase the intra-cellular level of branched chain keto acids derived from L-leucine, L-isoleucine, and L-valine to neutralize and detoxify hydrogen peroxide.

* * * * *

UNITED STATES PATENT AND TRADEMARK OFFICE
CERTIFICATE OF CORRECTION

PATENT NO.    : 6,149,924
DATED         : November 21, 2000
INVENTOR(S)   : Harbhajan S. Paul It is certified that error appears in the above-identified patent and that said Letters Patent is hereby corrected as shown below:

The title page should be deleted and substitute therefore the attached title page.

Title page,
Item [56], OTHER PUBLICATIONS, "Ghadially, Ruby et al.," reference, please replace "Journal of Clinical Investigation, Inc.," with -- Journal of Clinical Investigation, --.
"Paul, Harbhajan S. et al.," reference, please replace "ocidation" with -- oxidation --.
Please replace "American Physiological Society" with -- American Journal of Physiology --.
"Yosipovitch, Gil et al.," reference, please replace "Surgace" with -- Surface --.

Drawings,
Please replace the first page of Figure 1 with the following first page of figure 1 as shown below:

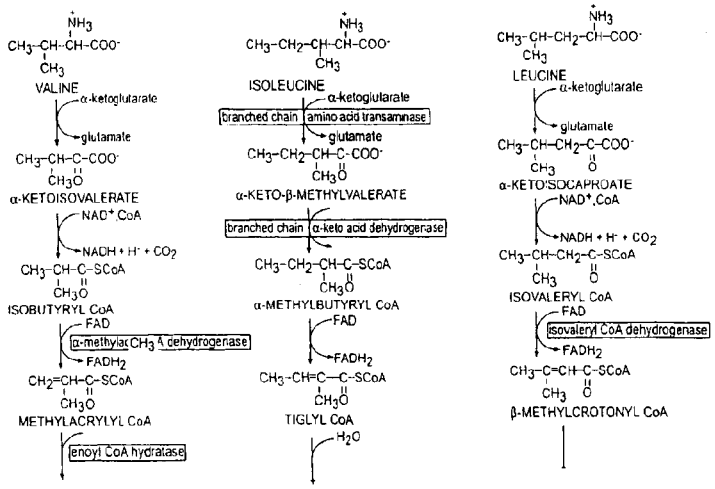

United States Patent [19]

Paul

[11] Patent Number: 6,149,924
[45] Date of Patent: Nov. 21, 2000

[54] COMPOSITION FOR ENHANCING LIPID PRODUCTION, BARRIER FUNCTION, HYDROGEN PEROXIDE NEUTRALIZATION, AND MOISTURIZATION OF THE SKIN

[75] Inventor: Harbhajan S. Paul, Wexford, Pa.

[73] Assignee: Biomed Research & Technologies, Inc., Wexford, Pa.

[21] Appl. No.: 09/118,909

[22] Filed: Jul. 20, 1998

[51] Int. Cl.$^7$ ............................................. A61K 7/00
[52] U.S. Cl. ................. 424/401; 424/450; 424/484; 514/2; 514/42
[58] Field of Search ............................ 424/401, 420, 424/484; 512/2, 42

[56] References Cited

U.S. PATENT DOCUMENTS

| | | | |
|---|---|---|---|
| 4,201,235 | 5/1980 | Ciavatta | 132/7 |
| 4,456,596 | 6/1984 | Schaeffer | 424/180 |
| 4,495,079 | 1/1985 | Good | 252/106 |
| 4,732,892 | 3/1988 | Sarpotdar et al. | 514/178 |
| 4,760,096 | 7/1988 | Sakai et al. | 514/847 |
| 4,859,653 | 8/1989 | Morelle elt al. | 514/2 |
| 5,091,171 | 2/1992 | Yu et al. | 424/642 |
| 5,175,190 | 12/1992 | Burton et al. | 514/560 |
| 5,204,099 | 4/1993 | Barbier et al. | 424/301 |
| 5,385,938 | 1/1995 | Yu et al. | 514/557 |
| 5,425,954 | 6/1995 | Thompson et al. | 424/401 |
| 5,470,880 | 11/1995 | Yu et al. | 514/574 |
| 5,472,698 | 12/1995 | Rawlings et al. | 424/401 |
| 5,520,991 | 5/1996 | Eustatiu | 424/195.1 |
| 5,561,158 | 10/1996 | Yu et al. | 514/557 |
| 5,569,461 | 10/1996 | Andrews | 424/405 |
| 5,614,556 | 3/1997 | Cavazza et al. | 514/556 |
| 5,643,899 | 7/1997 | Elias et al. | 514/171 |
| 5,658,580 | 8/1997 | Mausner | 424/401 |
| 5,681,853 | 10/1997 | Yu et al. | 514/557 |
| 5,866,537 | 2/1999 | Bianchi | 514/2 |

FOREIGN PATENT DOCUMENTS

| | | |
|---|---|---|
| 0 722 715 | 7/1996 | European Pat. Off. |
| 2 581 872 | 11/1986 | France |
| 2 694 692 | 2/1994 | France |
| 2 697 750 | 5/1994 | France |
| WO 96/36348 | 11/1996 | WIPO |

OTHER PUBLICATIONS

XP-002118778, STN, File Supplier Karlsruhe, DE, File Chemical Abstracts, vol. 66, *American Chemical Soc.*, 1999.
Patent Abstracts of Japan, 61289016 vol. II, No. 159.
Bonte, Frederic et al., "Analysis of all stratum corneum lipids by automated multiple development high performance thin–layer chromatography", *Journal of Chromatography B*, vol. 664; pp. 311–316,(1995).
Ghadially, Ruby et al., "Decreased Epidermal Lipid Synthesis Accounts for Altered Barrier Function in Aged Mice", *Journal of Investigative Dermatology*, vol. 106(5); pp. 1064–1069,(1996).

(List continued on next page.)

*Primary Examiner*—Jose' G. Dees
*Assistant Examiner*—Michael A. Willamson
*Attorney, Agent, or Firm*—Foley & Lardner

[57] ABSTRACT

Increased production of skin lipids, increased barrier function, hydrogen peroxide neutralization, prevention of loss of the natural moisturizing factor from the stratum corneum and moisturization of the skin is provided by a topically applicable composition which includes one or more components selected from the group consisting of branched chain amino acids, derivatives of branched chain amino acids and mixtures thereof, which one or more components are capable of being catabolized in epidermal cells to form lipid precursors for epidermal lipid synthesis. The composition can also include one or more enzyme activators which increase the rate of catabolism of the one or more components.

27 Claims, 4 Drawing Sheets

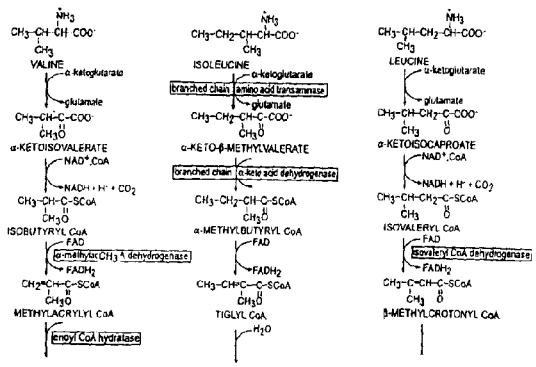

UNITED STATES PATENT AND TRADEMARK OFFICE
CERTIFICATE OF CORRECTION

PATENT NO. : 6,149,924
DATED : November 21, 2000
INVENTOR(S) : Harbhajan S. Paul It is certified that error appears in the above-identified patent and that said Letters Patent is hereby corrected as shown below:

Column 11,
Line 60, please replace "Boor" with -- $B_6$ or -- and on the same line, replace "intracellulary" with -- intracellularly --.

Column 21,
Line 12, please replace "cases" with -- casts --.
Line 51, please replace "B," with -- $B_1,$ --.

Column 22,
Line 32, please replace "in crease" with -- increase --.

Signed and Sealed this

First Day of July, 2003

JAMES E. ROGAN
*Director of the United States Patent and Trademark Office*